(12) United States Patent
Laugero et al.

(10) Patent No.: US 7,671,023 B2
(45) Date of Patent: Mar. 2, 2010

(54) AMYLIN AGONIST FOR TREATING DEPRESSION, ANXIETY DISORDER AND SCHIZOPHRENIA

(75) Inventors: Kevin D. Laugero, Davis, CA (US); Michael R. Hanley, San Diego, CA (US); Christine M. Mack, San Diego, CA (US); David G. Parkes, Del Mar, CA (US); Andrew A. Young, Rancho Sante Fe, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/910,206

(22) PCT Filed: Mar. 31, 2006

(86) PCT No.: PCT/US2006/012601

§ 371 (c)(1),
(2), (4) Date: Feb. 28, 2008

(87) PCT Pub. No.: WO2006/105527

PCT Pub. Date: Oct. 5, 2006

(65) Prior Publication Data

US 2008/0287355 A1    Nov. 20, 2008

Related U.S. Application Data

(60) Provisional application No. 60/666,681, filed on Mar. 31, 2005, provisional application No. 60/667,335, filed on Mar. 31, 2005, provisional application No. 60/675,441, filed on Apr. 28, 2005, provisional application No. 60/760,583, filed on Jan. 20, 2006.

(51) Int. Cl.
*A61K 38/00* (2006.01)
*A01N 37/18* (2006.01)

(52) U.S. Cl. .......................................... 514/12; 514/2

(58) Field of Classification Search ........................ None
See application file for complete search history.

(56) References Cited

U.S. PATENT DOCUMENTS

| 5,234,906 | A | 8/1993 | Young |
| 5,686,411 | A | 11/1997 | Gaeta |
| 5,998,367 | A | 12/1999 | Gaeta |
| 6,087,334 | A | 7/2000 | Beeley |
| 6,114,304 | A | 9/2000 | Kolterman |
| 6,410,511 | B2 | 6/2002 | L'Italian |
| 6,610,824 | B2 | 8/2003 | Gaeta |

FOREIGN PATENT DOCUMENTS

| WO | WO03/010146 | 5/1993 |
| WO | WO2006/042242 | 4/2006 |
| WO | WO2006/083254 | 8/2006 |
| WO | WO2006/105345 | 10/2006 |

OTHER PUBLICATIONS

Bouwknecht et al., 2007, Neuroscience and Behavioral Reviews, 31, pp. 41-59.*
Swerdlow et al., 2008, Psychopharmacology, 199, pp. 331-388.*
U.S. Appl. No. 60/617,468, filed Oct. 8, 2004, Mary Erickson.
U.S. Appl. No. 11/665,675.
Chrousos, G.P. "The Role of Stress and the Hypothalamic—Pituitary—Adrenal Axis" (2000) Int. J. Obes. Relat. Metab. Disord. 24:S50-S-55.
Dallman, Mary F. et al., "Corticotropin-Releasing Factors, Corticosteroids, Stress . . . " (2002) Hormones, Brain and Behavior San Diego, CA USA Acad. Press pp. 571-631.
Dallman, Mary F., "Chronic Stress and Obesity: A New View . . . ", Proc. Natl. Acad. Sci. USA (2003) 100:11696-11707.
Dunn et al., "Physiological and Behaviorial Responses to Corticotropin . . . " (1990) Brain Research, 15:71-100.
Grammatopoulous et al., "Role of Corticotropin-Releasing Hormone in Onset of Labour" (1999) Lancet 354:1546-1549.
Halford, Jason et al., "The Psychopharmacology of Appetite: . . . " (2003) Current Medicinal Chemistry CNS Agents, Vo. 3, N4.4, pp. 283-310.
Heinrichs et al. "Corticotropin-Releasing Factor Antagonists . . . " (1999) Bailleres Best Pract. Res. Clin. Indocrinol. Metab. 13:541-554.
Koob, "Corticotropin-Releasing Factor, Norepinephrine, and Stress" (1999) Biol. Psychiatry 46:1167-1180.
Krahn et al., "CRF Antagonist Partially Reverses CRF- and Stress-Induced . . . " (1986) Brain Research Bulletin 17:285-289.
Laugero et al., "Sucrose Ingestion Normalizes Central Expression of Corticotropin . . . " (2001) Endocrinology 142:2796-2804.
Laugero et al., "Corticosterone Infused Intracerebroventricularly Inhibits Energy" (2002) Endocrinoology 143:4552-4562.
Laugero et al., "Reinterpretation of Glucocorticoid Feedback in the HPA Axis . . . " (2004) Vitamins and Hormones, vol. 68, Litwack (ed.).
Morley et al., "Effects of Amylinon Appetite Regulationa nd Memory" (1995) Canadian Journ. of Physiol. and Parmac., Ottawa Ont CA V. 73:1042-1046.
Peek et al., "Hypercortisolism and Obesity" 1995 Ann. N.Y. Acad. Sci. 771:665-676.
Ratner, R.E. et al., "Adjunctive Therapy with the Amylin Analogue . . . " (2002) Diabetes Technology & Therapeutics, vol. 4#1 pp. 51-61.
Sarnyai et al., "The Role of Corticotropin-Releasing Factor in Drug Addiction" (2001) Pharmacol. Rev. 53:209-243.
Smagin et al., "Prevention of stress-induced weight loss by third ventricle CRF receptor antagonist" (1999) Am. J. Physiol. 276:R1461-1468.
Wong et al., "Pronounced and Sustained Central Hypernoradrenergic Function in Major Depression with . . . " (2000) Proc. Natl. Acad. Sci USA 97:325-330.

* cited by examiner

*Primary Examiner*—Olga N Chernyshev

(57) ABSTRACT

Methods and compositions for treating psychiatric diseases and disorders are disclosed. The methods provided generally involve the administration of an amylin or an amylin agonist to a subject in order to treat psychiatric diseases and disorders, and conditions associated with psychiatric diseases and disorders.

3 Claims, 5 Drawing Sheets

AMYLIN AGONIST FOR TREATING DEPRESSION, ANXIETY DISORDER AND SCHIZOPHRENIA

CROSS-REFERENCE TO RELATED APPLICATIONS

This application is a national stage application of International PCT Application No. PCT/US2006/012601, filed Mar. 31, 2006, now published as WO2006/105527, which claims priority to U.S. Provisional Application No. 60/666,681, filed Mar. 31, 2005; U.S. Provisional Application No. 60/667,335, filed Mar. 31, 2005; U.S. Provisional Application 60/675,441, filed Apr. 28, 2005 and U.S. Provisional Application No. 60/760,583, filed Jan. 20, 2006; priority to all of which is hereby claimed. All applications are hereby incorporated by reference in their entireties and for all purposes.

TECHNICAL FIELD

This disclosure is in the medical field and in particular to the fields of psychology and psychiatry, as well as health, diet and nutrition.

BACKGROUND

Psychiatric diseases and disorders (also referred to as mental illnesses or disorders) are described in resources such as the American Psychiatric Association's *Diagnostic and Statistical Manual of Mental Disorders*, or DSM-IV. Broad categories of mental disorders include, but are not limited to, mood disorders, anxiety disorders, schizophrenia and other psychotic disorders, substance-related disorders, sleep disorders, somatoform disorders, and eating disorders. Examples of mood disorders include bipolar and depression. Other conditions falling within the broader category of disorders described above can be found in the DSM-IV, which is incorporated by reference in its entirety. These are debilitating illnesses that affect millions of people and involve astronomical costs, in terms of treatment, lost productivity, and emotional toll.

In 2001, the National Institute of Mental Health published a summary of statistics describing the prevalence of mental disorders in America. In the report, it estimated that 22.1% of Americans ages 18 and older suffer from a diagnosable mental disorder in a given year (Reiger et al. (1993) *Archives of General Psychiatry* 50:85-94). When applied to the 1998 U.S. Census, the number of people affected was 44.3 million.

Depressive disorders can encompass, among others illnesses, major depressive disorder, dysthymic disorder and bipolar disorder. About 9 to 9.5 percent of the U.S. population ages 18 and older have a depressive condition. It has been reported that the direct cost of depressive disorders is about $80 billion, with two-thirds of it being borne by businesses. The indirect costs associated with depressive disorders, such as lost productivity, are harder to calculate because of events such as "presenteeism," described as people at work but limited in their ability to produce or participate (Durso, Employee Benefit News, December 2004).

Another psychiatric condition is anxiety disorders. These disorders can include panic disorder, obsessive-compulsive disorder, post-traumatic stress disorder generalized anxiety disorder, and phobias. Approximately 19.1 million American adults ages 18 to 54 (about 13.3% of people in this age group in a given year) have an anxiety disorder.

Another common psychiatric condition is eating disorders. There are three main types, anorexia nervosa, bulimia nervosa, and binge-eating disorders. These are psychiatric conditions are often linked to perceived notions about body image and are usually independent of actual body weight or body mass index. The mortality of people with anorexia has been estimated at 0.56 percent per year, or approximately 5.6 percent per decade, which is about 12 times higher than the annual death rate due to all causes of death among females ages 15-24 in the general population (Sullivan (1995) *American Journal of Psychiatry* 152:1073-1074). It should be noted that psychiatric illnesses usually present with elements of other psychiatric disorders.

Another psychiatric condition is schizophrenia. In a given year, over 2 million people are clinically diagnosed with schizophrenia, and there is a lifetime prevalence of this disease in approximately 1% of the U.S. population. Schizophrenia is a chronic, debilitating disease that leaves an estimated 75% of treated patients without ever achieving complete recovery. Treatment of schizophrenia with the newer (atypical) antipsychotic medications frequently comes with the side effect of weight gain and possibly diabetes.

Exemplary types of schizophrenia include paranoid schizophrenia. These persons are very suspicious of others and often have grand schemes of persecution at the root of their behavior. Hallucinations, and more frequently delusions, are a prominent and common part of the illness. Persons with disorganized schizophrenia (Hebephrenic Schizophrenia) are verbally incoherent and may have moods and emotions that are not appropriate to the situation. Hallucinations are not usually present with disorganized schizophrenia. Catatonic schizophrenia is where a person is extremely withdrawn, negative and isolated, and has marked psychomotor disturbances. Residual schizophrenia is where a person is not currently suffering from delusions, hallucinations, or disorganized speech and behavior, but lacks motivation and interest in day-to-day living. Schizoaffective disorder is where a person has symptoms of schizophrenia as well as mood disorder such as major depression, bipolar mania, or mixed mania. Undifferentiated schizophrenia is where conditions meet the general diagnostic criteria for schizophrenia but do not conform to any of the above subtypes, or there are features of more than one of the subtypes without a clear predominance of a particular set of diagnostic characteristics.

Psychiatric diseases and disorders can be found in any age group. Accordingly, these disorders can be found in young adults and adults (defined herein as those aged 65 or under) as well as infants, children, adolescents, and the elderly (defined herein as over the age of 65). In fact, certain segments of the population may be particularly prone to having a condition, such as eating disorders in adolescents and young adults. The elderly may be particularly susceptible to conditions such as depression.

Current treatments include psychosocial and behavioral therapy, electroconvulsive therapy, and/or medication. A common form of treatment for psychiatric illnesses, or at least a component of the treatment, is the administration of medication. Needed in the art are molecules that (1) effectively treat those patients resistant to the current antidepressants (e.g., tricyclics, monoamine oxidase inhibitors, selective serotonin reuptake inhibitors) (2) effectively treat depression, anxiety, schizophrenia, or other psychiatric diseases or disorders without the unwanted side effects of the current pharmaceuticals, (3) have a faster onset of therapeutic action, and/or (4) improve physical co-morbidities (e.g., diabetes, pain, weight gain) that often present with and make more difficult the treatment of psychiatric illnesses, such as depression, anxiety, and schizophrenia to name just a few.

All references cited herein are incorporated by reference in their entirety.

SUMMARY

In one general aspect, methods provided include the use of amylin and its agonists, analogs, or derivatives in therapeutically effective amounts for the treatment of a psychiatric disorder. In certain embodiments, the psychiatric disorder is a mood disorder, an anxiety disorder, schizophrenia or other psychotic disorder, a substance-related disorder, a sleep disorder, a somatoform disorder, and/or an eating disorder. In certain embodiments, the psychiatric disorder is depression or bipolar disorder. In certain embodiments, the psychiatric disorder is an obsessive-compulsive disorder. In certain embodiments, methods provided may not include treating an eating disorder. In other embodiments, methods provided may not include treating anorexia. In certain embodiments, methods provided may not include a somatoform disorder. In certain embodiments, amylin and its agonists, analogs, or derivatives are used to treat the underlying psychiatric condition of an eating disorder. In certain embodiments, amylin and its agonists, analogs, or derivatives are used to treat the underlying psychiatric condition of a somatoform disorder. In certain embodiments, amylin agonists may not include a calcitonin and/or a calcitonin-gene-related peptide (CGRP). In still other embodiments, amylin agonists may not include an analog of calcitonin and/or CGRP.

In still another aspect, methods provided include treating a psychiatric disorder in a subject desirous of, or in need of, treatment comprising administering a therapeutically effective amount of an amylin, its agonists, analogs, or derivatives to the subject. In certain embodiments, the subject is overweight. In other embodiments, the subject is obese. In still other embodiments, the subject is lean, not overweight or obese. In still other embodiments, the subject has a metabolic condition. In yet other embodiments, the subject has diabetes, metabolic syndrome, impaired glucose tolerance, or insulin resistance. In other embodiments, amylin and its agonists, analogs, or derivatives are beneficial in aiding the subject with their ability to modify food preferences or food cravings.

In another general aspect, methods provided herein include administration of a therapeutically effective amount of amylin, or its agonist, analogs, and derivatives, in combination with a conventional treatment for psychiatric disorders. In certain embodiments, the combination includes the administration of electroconvulsive therapy (ECT). In other embodiments, the combination includes the administration of another psychiatric medication. In still other embodiments, the psychiatric medication is one or more of tricyclic antidepressants, monoamine oxidase inhibitors (MAOIs), selective serotonin reuptake inhibitors (SSRIs), serotonin and noradrenaline reuptake inhibitors (SNRIs), herbal antidepressants (e.g., St John's Wort or *Hypericum*), or second generation antipsychotic medications (SGAs).

In another general aspect, methods provided herein include treating an unwanted side effect of another psychiatric medication comprising administering a therapeutically effective amount of amylin, or its agonist, analogs, and derivatives, to a subject in need thereof. In certain embodiments, the other psychiatric medication is a second generation antipsychotic medication. In certain embodiments, the unwanted side effect of the other psychiatric medication is weight gain. In other embodiments, the unwanted side effect of the other psychiatric medication is diabetes.

In another general aspect, methods provided include treating a psychiatric disorder comprising administering a therapeutically effective amount of a compound that modulates behavioral pathways through its modulatory actions on metabolic pathways or function, including but not limited to glucose metabolism, lipid metabolism, protein metabolism, and total energy metabolism. In certain embodiments, the behavioral pathway is a corticotropin-releasing factor (CRF) pathway that modulates at least one component of the hypothalamic-pituitary-adrenal axis. In one embodiment, the behavioral pathway is a dopamine pathway. In other embodiments, the behavioral pathway is the $5HT_{1A}$ pathway or any pathway comprising the serotonergic system. In certain embodiments, the metabolic or behavioral pathway is any one of glucoregulatory, glucocorticoid responsive, or stress responsive. In certain embodiments, the compound is an amylin or its agonist, analog or derivative.

In still another aspect, methods provided include treating a psychiatric disorder by administering a therapeutically effective amount of a compound that modulates behavioral pathways through its modulatory actions on food intake. In certain embodiments the compound is amylin or its agonist, analog or derivative.

In another aspect, the disclosure provides for the use of an amylin, its agonists, analogs, or derivatives for manufacture of a medicament useful for treating psychiatric diseases and disorders described herein. In another aspect, the disclosure provides for the use of an amylin, its agonists, analogs, or derivatives for manufacture of a medicament useful for treating unwanted side effects of another psychiatric medication, for example, a second generation antipsychotic medication.

DETAILED DESCRIPTION

Figure 1A:
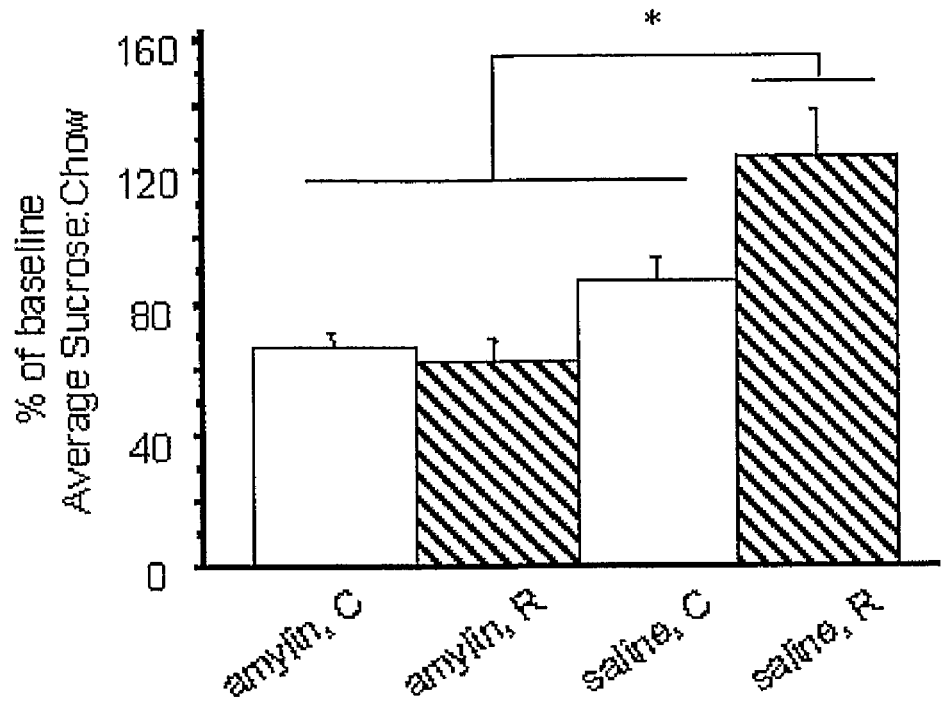
FIGS. 1A and 1B are graphs depicting effects of amylin on stress-induced feeding. In these graphs, R indicates animals subjected to restraint stress and C indicates control animals not subjected to restraint stress.

It has now been discovered that amylin, amylin agonists, amylin analogs, amylin agonist analogs, amylin derivatives, or a combination thereof, may be able to modulate the stress systems and/or the actions of CRF and/or glucocorticoids (GC), thereby presenting novel pharmacotherapeutic options. As demonstrated herein, amylin administration appears to reduce or protect against stress and it effects (e.g., anxiety, obsessive-compulsive behavior, depression, psychosis, changes in eating behavior). We also demonstrate herein that, in specific animal behavioral tests, amylin administration results in behavioral effects that include anti-stress, anxiolytic, antidepressant, and antipsychotic actions.

In exploring new medical treatments, it was noted that a number of metabolic pathologies (e.g., diabetes, obesity) are associated with behavioral dysfunction (e.g., major depression, schizophrenia). Although these diseases are generally believed to be co-morbid, there is recent evidence suggesting that the behavioral and metabolic alterations are physiologically linked in many cases (Laugero et al. (2001) *Endocrinology* 142:2796-2804; Laugero et al. (2002) *Endocrinology* 143:4552-4562; Dallman et al. (2003) *Proc. Natl. Acad. Sci. USA* 100:11696-11701; Laugero (2004) *Vitamins and Hormones*, Volume 68, Litwack (ed.)). A common link between these seemingly disparate disease states may be chronic stress and the associated changes in brain CRF and the adrenocortical steroid hormones, GC.

The CRF and GC molecules play a critical role in modulating behavioral, neuroendocrine, autonomic, and metabolic function under normal and stressful conditions. Chronic stress and the induction of expression and activity of these molecules are highly associated with behavioral diseases like anxiety and depression, and also with some obesities and diabetes. There is evidence that links CRF and adrenocortical abnormalities to the metabolic syndrome, autoimmune inflammatory disorders, acute and chronic neurodegeneration, sleep disorders, chronic pain, eating disorders, chronic anxiety disorder, and major depression (Wong et al. (2000) *Proc. Natl. Acad. Sci. USA* 97:325-330; Sarnyai et al. (2001) *Pharmacol. Rev.* 53:209-243; Heinrichs et al. (1999) *Baillieres Best Pract. Res. Clin. Endocrinol. Metab.* 13:541-554; Chrousos (2000) *Int. J. Obes. Relat. Metab. Disord.* 24:S50-S55; Peek et al. (1995) *Ann. N.Y. Acad. Sci.* 771:665-676; Grammatopoulos et al. (1999) *Lancet* 354:1546-1549; Dallman et al (2003) *Proc. Natl. Acad. Sci. USA* 100:11696-11701).

As demonstrated herein, amylin is shown to share properties of anxiolytic, antidepressant, and antipsychotic agents in behavioral testing. Thus, it has now been discovered that amylin and amylin agonists may have the surprising ability to treat psychiatric disorders. Psychiatric disorders that can be treated include mood disorders, anxiety disorders, schizophrenia and other psychotic disorders, substance-related disorders, sleep disorders, somatoform disorders, and eating disorders. These compounds may be particularly effective in treating psychiatric disorders that have elements of metabolic disturbances, e.g., eating disorders, or in treating patients with a psychiatric disorder or those with a psychiatric disorder and who also suffer from a metabolic disturbance.

More particular types of the above named disorders can be found in the DSM-IV. The following are only examples of disorders that may be treated by the methods disclosed herein. Examples include mood disorders that may include depressive disorders and bipolar disorders. They can further be characterized as major depressive disorders, dysthymic disorder, bipolar I disorder, bipolar II disorder, cyclothymic disorder, bipolar disorder not otherwise specified, mood disorders due to a medical condition, substance-induced mood disorder, or mood disorder not otherwise specified. Anxiety disorders can include panic disorder, specific phobia, social phobia, obsessive-compulsive disorder, posttraumatic stress disorder, acute stress disorder, generalized anxiety disorder, anxiety disorder due to a medical condition, substance induced anxiety disorder and anxiety disorder not otherwise specified.

Substance-related disorders include substance dependence, substance addiction, substance-induced anxiety disorder, and substance-induced mood disorder. Substance dependence and addiction can occur with a variety of substances, including but not limited to, alcohol, nicotine, cocaine, opioids, narcotics, hallucinogens, amphetamines, phencyclidines, phencyclidine-like substances, inhalants, and sedatives. Substance-induced anxiety disorder can occur in response to substances which include, but not limited to, caffeine, cannabis, cocaine, hallucinogens, amphetamines, phencyclidines, phencyclidine-like substances, and inhalants. Substance-induced mood disorder can occur in response to substances which include, but not limited to cocaine, hallucinogens, opioids, amphetamines, phencyclidines, phencyclidine-like substances, and inhalants. Substance-related disorders can occur in response to one substance or to a combination of substances, such as in polysubstance-related disorder.

In some embodiments, methods provided include the treatment of medication-induced psychiatric disorders or psychiatric disorders that result from treatment of a disease. For example, hedonistic homeostatic dysregulation is a neuropsychological behavioral disorder recognized in patients with Parkinson's disease undergoing dopamine replacement therapy. Dopamine replacement therapy in these patients appears to stimulate central dopaminergic pathways and lead to a behavioral disorder with some similarities to that associated with stimulant addiction. Giovannoni et al. (2000) *J. Neurol. Neurosurg. Psychiatry* 68:423-428.

Eating disorders can include anorexia nervosa, bulimia nervosa, and eating disorders not otherwise specified. These eating disorders may include binge eating. In certain embodiments, methods provided are drawn to the treatment of the psychiatric illness associated with the eating disorder. In other embodiments, methods provided do not include the treatment of eating disorders. In certain embodiments, methods provided do not include the treatment of anorexia. In other embodiments, methods provided may be used for treating the psychiatric illness associated with anorexic patients. In certain embodiments, methods provided do not include the treatment of binge eating.

In some embodiments, methods provided can be used to treat subjects experiencing intermittent excessive behaviors (IEB). IEB characterize a variety of disorders including, binge eating, substance abuse, alcoholism, aberrant sexual conduct, and compulsive gambling. IEB occur when occasional normal behavioral excess is transformed into repetitive, intermittent, maladaptive behavioral excess. Corwin (2006) *Appetite* 46:11-15.

In certain embodiments, methods provided may not include the treatment of somatoform disorders. In certain embodiments, methods provided may include somatoform disorders but do not include the treatment of physical pain. In still other embodiments, methods provided may include the treatment of the psychiatric illness associated with pain.

In one general aspect, it is contemplated that compounds that reduce or moderate stress, or regulate the stress pathway, may be useful as pharmacotherapeutic agents. In another general aspect, it is contemplated that compounds that can affect or regulate metabolic disturbances as well as psychiatric or behavioral processes would be useful as pharmacotherapeutic agents. In another general aspect, it is contemplated that compounds that can attenuate or reverse metabolic disturbances would be useful as pharmacotherapeutic treatments of psychiatric diseases or disorders. It is contemplated that compounds useful in the methods provided may be amylin, amylin agonists, amylin analogs, and amylin derivatives. In certain embodiments, amylin agonists may not include calcitonin and/or CGRP.

It is theorized that medicines that not only treat the psychiatric illness, but also alleviate the physical co-morbidities of the illness, would be expected to elicit an increased rate of treatment response and outcome success in patients with a psychiatric illness. Physical co-morbidities, like diabetes, exacerbate the morbidity that comes with psychiatric illness and lead to a reduction in treatment response. Amylin and its agonists may be particularly useful in the methods described herein because of its anti-diabetic, anti-obesigenic, and appetite suppressant effects. Amylin and its agonists may further be beneficial in aiding the subject with their ability to modify food preferences described in commonly-owned U.S. Pat. Application No. 60/666,681, filed on Mar. 31, 2005, and PCT application PCT/US06/11768, filed 31 Mar. 2006, the contents of each are incorporated by reference in its entirety. These effects may increase the rate of treatment response and outcome success in certain patient populations who suffer a psychiatric illness and who exhibit obesity, obesity-related disease, or eating disorders (e.g., diabetes, metabolic syndrome, obesity, Cushing's syndrome, Cushing's disease, atypical major depression, schizophrenia, seasonal affective disorder, polycystic ovary syndrome, post-traumatic stress disorder, night eating syndrome, bulimia nervosa, binge eating disorder, and chronic fatigue syndrome). In certain embodiments, the methods do not include treatment of anorexia. In other embodiments, the methods include treating the psychiatric illness associated with anorexia.

Still another general aspect includes the use of the naturally occurring and peripherally secreted amylin peptide or an amylin agonist, analog, or derivative, for the treatment of psychiatric disorders. In some embodiments, methods for psychiatric disorders in a subject are provided, wherein the method comprises administering to a subject in need thereof, an amylin or an amylin agonist, analog, or derivative in an amount effective to treat the psychiatric disorder. In some instances, the psychiatric disorders are of natural or unidentified etiology. In some instances, the psychiatric disorder may result from medication for or treatment of a different disease. Accordingly, in some embodiments, methods for treating medication-induced psychiatric disorders or psychiatric disorders that result from treatment of a disease in a subject are provided, wherein the method comprises administering to a subject in need thereof an amylin or an amylin agonist, analog, or derivative in an amount effective to treat the psychiatric disorder. Because the amylin peptide is a naturally secreted hormone, it may reduce the side effect profile commonly present in patients receiving the currently prescribed treatments and pharmaceuticals for psychiatric disorders. Another general aspect includes the use of compounds that can treat both the psychiatric disease and metabolic disturbances present in a subject.

Amylin, amylin agonists, amylin analogs, or amylin derivatives may also be superior to some other antidepressant, anxiolytic, and/or antipsychotic agents, as it does not promote weight gain and, in fact, may induce weight loss. This attribute of amylin may lead to greater compliance among patients being treated for psychiatric disease.

It is further contemplated that amylin or its agonists, analogs or derivatives, may be used in conjunction with other psychiatric medications or therapies, such as those conventionally used to treat psychiatric disease, such as tricyclic antidepressants and the monamine oxidase inhibitors (MAOIs), selective serotonin reuptake inhibitors (SSRIs), serotonin and noradrenaline reuptake inhibitors (SNRIs), herbal antidepressants (e.g., St John's Wort or *Hypericum*), second generation antipsychotic medications (SGAs), psychoanalysis, cognitive-behavioral therapy, and interpersonal therapy. When used in conjunction with other psychiatric medications or therapies, administration of the amylin or amylin agonist may occur concurrently or sequentially with the other psychiatric medications or therapies. For example, the amylin or amylin agonist may be administered during the same time period as the other psychiatric medication, during an overlapping time period as the other psychiatric medication, or in a time period that does not overlap with administration of the other psychiatric medication. As a combination or add-on therapy, the beneficial qualifies of an amylin or amylin agonist may counteract or moderate one or more of the unwanted side effects of currently available medications, e.g., weight gain, diabetes.

For example, SGAs are effective therapeutics for the treatment of symptoms associated with schizophrenia and related psychotic conditions. Despite these advances in treating the psychiatric condition, accumulating clinical data have revealed an association between the use of SGAs and weight gain, diabetes, and dyslipidemia (American Diabetes Association et al. (2004) *Diabetes Care* 27: 596-601). Weight gain may be one contributing factor to a patient's non-compliance with his medication. So, as good as any medication may be, it does not provide any benefit to a patient that is not taking it, or not taking it properly. Exemplary SGAs such as clozapine and olanzapine have been identified as being likely to produce weight gain; in addition, these two SGAs have also been associated with increased risk for both diabetes and dyslipidemia. The ability of amylin to effectively reduce body weight gain induced by clozapine treatment is demonstrated herein in Example 3. In addition, amylin and amylin agonists are also able to treat or aid in the treatment of diabetes and dyslipidemia. The amylin agonist, pramlintide, has been approved by the FDA as an adjunct therapy to insulin in the treatment of diabetes (type 1 and type 2). Accordingly, when used with other psychiatric medications, amylin and amylin agonists may not only provide an additional treatment to the psychiatric condition, but also be able to counteract at least a negative side effect of those other psychiatric medications.

As used herein, a "subject" may include any mammal, including humans. A "subject" may also include pets (e.g., dogs, cats, horses), as well as other animals. Subjects may have at least one of the psychiatric disorders described herein. Subjects who may benefit from the methods disclosed herein may be overweight or obese; however, they may also be lean. They may have a metabolic disorder or condition in addition to a psychiatric disorder. Exemplary metabolic disorders include diabetes, metabolic syndrome, insulin-resistance, and dyslipidemia. Subjects can be of any age. Accordingly, these disorders can be found in young adults and adults (defined herein as those aged 65 or under) as well as infants, children, adolescents, and the elderly (defined herein as over the age of 65). In fact, certain segments of the population may be particularly prone to having a particular condition, such as eating disorders in adolescents and young adults. The elderly may be particularly susceptible to conditions such as depression.

As used herein, and as well-understood in the art, "treatment" is an approach for obtaining beneficial or desired results, including clinical results. "Treating" or "palliating" a disease, disorder, or condition means that the extent, undesirable clinical manifestations of a condition, or both, of a disorder or a disease state are lessened and/or time course of the progression is slowed or lengthened, as compared to not treating the disorder. For purposes of the methods disclosed herein, beneficial or desired clinical results include, but are not limited to, alleviation or amelioration of one or more symptoms, diminishment of extent of disorder, stabilized (i.e., not worsening) state of disorder, delay or slowing of disorder progression, amelioration or palliation of the disorder, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the singular form "a", "an", and "the" includes plural references unless otherwise indicated or clear from context. For example, as will be apparent from context, "an" amylin agonist can include one or more amylin agonists.

Without wishing to be bound by theory, amylin may exert its psychiatric/behavioral effects by modulating GC-responsive sites (such as the brain) and impact functions that are normally modulated by GCs (e.g., CFR) expression and activity, behavior, autonomic nervous system activity, neuroendocrine function, and metabolism). Without wishing to be bound by theory, amylin, its agonists, analogs, or derivatives, may block or reduce the behavioral (e.g., anxiety, depression) and metabolic (e.g., feeding, obesigenic) effects of GCs, brain CRF, or chronic stress. In addition, amylin may have some antidepressant, anxiolytic, and/or antipsychotic activities that are not directed related to it's anti-diabetic or anti-obesity activities. Again, without wishing to be bound by theory, amylin may, in part, be working by modulating, or otherwise, affecting stress pathways and/or the CRF and/or GC regulatory actions on stress-mediated behavioral, autonomic, neuroendocrine, and metabolic responses.

Stress, GC, and CRF seem to have an intricate and complicated relationship in psychological and metabolic function. Stress has profound effects on neuroendocrine (e.g., hypothalamic-pituitary-adrenal (HPA) axis), autonomic, behavioral (e.g., anxiety, depression, substance abuse, feeding), and metabolic (e.g., fat deposition, energy utilization) function in man and animals (Dallman et al. (2002) *Hormones, Brain, and Behavior* pp 571-631, San Diego, Calif. USA: Academic Press.). All of these effects are modulated by GCs. The neuropeptide CRF mediates many of the stress-induced responses, including acute inhibition of food intake and anxiety (Krahn et al (1986) *Brain Research Bulletin* 17:285-289; Dunn et al. (1990) *Brain Res. Brain Res. Rev.* 15:71-100; Smagin et al. (1999) *Am. J. Physiol.* 276:R1461-1468; Koob (1999) *Biol. Psychiatry* 46:1167-1180). GC and CRF activity are tightly interdependent and, together, make up a functional and well-described physiological system that controls behavioral, autonomic, neuroendocrine, and metabolic function (Dallman et al. (2003) *Proc. Natl. Acad. Sci. USA* 100:11696-11701).

Disruptions in the GC and CRF relationship, such as those caused by stress, can have profound effects on health. Through the central actions of chronically elevated glucocorticoid hormones (cortisol in man, corticosterone in rodents), chronic stress promotes palatable feeding (e.g., simple sugar, fat). When palatable food is available, as it abundantly is in modern societies, chronic stress increases the proportion of palatable calories consumed (Pecoraro et al. (2004) *Endocrinology* 145:3754-3762; Laugero (2004) *Vitamins and Hormones*, Volume 68. Ed. Gerald Litwack; Laugero et al. (2002) *Endocrinology* 143:4552-4562). The significance of this response, under the background of elevated GCs, is increased fat deposition in the abdominal or truncal region (Dallman et al. (2003) *Proc. Natl. Acad. Sci. USA* 100: 11696-11701), which is a significant and independent risk factor for the development of cardiovascular disease (Bjorntorp (1993) *Obesity Research* 1:206; Carr et al. (2004) *Diabetes* 53:2087-2094). In fact, endogenous GC elevation, as in Cushing's patients, or through exogenous administration, as in Lupus patients, cause metabolic syndrome (truncal obesity, insulin resistance, hypertension, hypertriglyceridemia) (Stewart (2003) The Adrenal Cortex, *Williams Textbook of Endocrinology*, $10^{th}$ edition, Saunders Publishing, U.S.). Furthermore, truncal obesity is characterized by increased glucocorticoid activity, and it has been hypothesized that, through the activation of adrenocortical synthesis and secretion of GCs, chronic stress plays a significant role in the development of truncal obesity and the metabolic syndrome (Bjorntorp (2001) *Obes. Rev.* 2:73-86; Rosmond et al. (2000) *Obes. Res.* 8:445-450; Bjorntorp (1997) *Nutrition* 13:795-803; Dallman et al. (2002) *Hormones, Brain, and Behavior* pp 571-631, San Diego, Calif. USA: Academic Press.; Dallman et al. (2003) *Proc. Natl. Acad. Sci. USA* 100:11696-11701).

Hyper- and hypo-cortisolemia are also well-documented features of psychiatric disease, and patients suffering from the metabolic syndrome show signs of abnormal cortisol secretion and are more likely to present with a psychiatric disease such as major depression. Chronic stress and the associated increase in central CRF activity are believed to play a critical role in the development of clinical depression, anxiety disorders, substance abuse, eating disorders, and metabolic syndrome (Chrousos et al. (2000) *Int. J. Obes. Relat. Metab. Disord.* 24:S50-S55; Koob (1999) *Biol. Psychiatry* 46:1167-1180). In fact, small molecule CRF antagonists are currently being investigated for their therapeutic actions in patients with major depression, general anxiety disorder, eating disorders, and other stress related pathologies.

Amylin is a hormone that is co-secreted with insulin from the pancreatic β-cell and that has numerous metabolic effects, including glucoregulatory actions. The glucoregulatory actions of amylin may be related to its effects on gastric emptying, suppression of inappropriately elevated postprandial glucagon secretion, and inhibition of food intake (Young (1997) *Curr. Opin. in Endocrinology and Diabetes* 4:282-290). An amylin agonist analog, pramlintide, is being developed for the treatment for type 1 and 2 diabetes (Baron et al (2002) *Curr. Drug Targets Immune Endocr. Metabol. Disord.* 2:63-82) and has recently been approved by the FDA for such use. Because of its anti-diabetic effects, amylin is also a good candidate for treating the metabolic syndrome. Moreover, amylin is a candidate for an anti-obesity drug for humans due to its effect on weight in animals (Mack et al. (2003) *Diabetes* 52 (Suppl. 1) A389).

Amylin agonists include amylin agonist analogs, examples of which are described in U.S. Pat. No. 5,686,411; U.S. Pat. No. 6,610,824; U.S. Pat. No. 5,998,367; U.S. Pat. No. 6,087,334; U.S. Provisional Application No. 60/617,468, filed Oct. 8, 2004; and PCT Application No. PCT/US2005/004631, all of which are incorporated herein by reference. In certain embodiments, methods provided may not include the use of calcitonins. In certain embodiments, the calcitonin is salmon calcitonin. In other embodiments, methods provided may not include the use of CGRP. In still other embodiments, methods provided may not include the use of analogs of CGRP or calcitonin. Accordingly, it is contemplated that methods provided may include a proviso that excludes CGRP, calcitonin, or their analogs.

By "amylin" is meant the human peptide hormone referred to as amylin and secreted from the beta cells of the pancreas, and species variations thereof, examples of which are described in U.S. Pat. No. 5,234,906, the contents of which are hereby incorporated by reference. More particularly, amylin is a 37-amino acid polypeptide hormone normally co-secreted with insulin by pancreatic beta cells in response to nutrient intake (see, e.g., Koda et al. (1992) *Lancet* 339: 1179-1180). In this sense, "amylin," "wild-type amylin," and "native amylin," i.e., unmodified amylin, are used interchangeably. Amylin is also sometimes referred to as "IAPP."

By "agonist" is meant a compound which elicits a biological activity of amylin, for example, having a potency better than amylin, or within five orders of magnitude (plus or minus) of potency compared to amylin, for example 4, 3, 2, or 1 order of magnitude, when evaluated by art-known measures such as, for example, receptor binding/competition studies as described herein.

In one embodiment, the term agonist refers to a compound which elicits a biological effect similar to that of native amylin, for example a compound (1) having activity in a food intake, gastric emptying, pancreatic secretion, or weight loss assay (PCT Application No. PCT/US2005/004631, filed on Feb. 11, 2005, and incorporated by reference) similar to the native human reference peptide, and/or (2) which binds specifically in a reference receptor assay or in a competitive binding assay with amylin. In the agonists will bind in such assays with an affinity of better than 1 μM, and, in another embodiment, with an affinity of better than 1-5 nM. Such agonists may comprise a polypeptide comprising an active fragment of amylin or a small chemical molecule. In some embodiments, an agonist is a peptide, not a small chemical molecule. It is, however, contemplated that in certain embodiments, salmon calcitonin, calcitonin, CGRP, and/or their respective analogs may be excluded from the scope of amylin agonist with proviso language. In certain embodiments, an amylin agonist is not a small chemical molecule and small chemical molecules may be excluded from the scope of amylin agonist with proviso language.

Agonists include amylin analogs and amylin derivatives. By "analog" is meant a peptide whose sequence is derived from that of amylin including insertions, substitutions, extensions, and/or deletions, having at least some amino acid identity to amylin or region of an amylin peptide. Analogs may have at least 50 or 55% amino acid sequence identity with a native amylin, or at least 70%, 80%, 90%, or 95% amino acid sequence identity with a native amylin. In one embodiment, such analogs may comprise conservative or non-conservative amino acid substitutions (including non-natural amino acids and L and D forms). Amylin agonist analogs are analogs as herein described and function as an amylin agonist.

A "derivative" is defined as a molecule having the amino acid sequence of a native amylin or analog, but additionally having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

Human amylin (hAmylin or h-amylin) has the following amino acid sequence: Lys-Cys-Asn-Thr-Ala-Thr-Cys-Ala-Thr-Gln Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). Rat amylin (rAmylin) has the following sequence: KCNTATCATQRLANFLVRSSNNLG-PVLPPTNVGSNTY (SEQ ID NO:2). The use of amylins from any species is contemplated.

Amylin agonists contemplated in the use in the methods disclosed herein include those described in U.S. Pat. Nos. 5,686,411, 6,114,304, and 6,410,511, and PCT Application Publication No. WO 93/10146, the contents of which are herein incorporated by reference in their entirety. Such compounds include those having formula I:

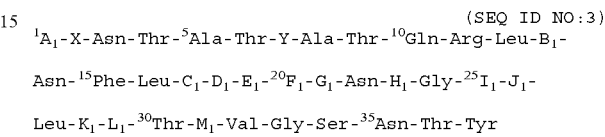

$^1$A$_1$-X-Asn-Thr-$^5$Ala-Thr-Y-Ala-Thr-$^{10}$Gln-Arg-Leu-B$_1$-Asn-$^{15}$Phe-Leu-C$_1$-D$_1$-E$_1$-$^{20}$F$_1$-G$_1$-Asn-H$_1$-Gly-$^{25}$I$_1$-J$_1$-Leu-K$_1$-L$_1$-$^{30}$Thr-M$_1$-Val-Gly-Ser-$^{35}$Asn-Thr-Tyr wherein A$_1$ is Lys, Ala, Ser or hydrogen;
B$_1$ is Ala, Ser or Thr;
C$_1$ is Val, Leu or Ile;
D$_1$ is His or Arg;
E$_1$ is Ser or Thr;
F$_1$ is Ser, Thr, Gln or Asn;
G$_1$ is Asn, Gln or His;
H$_1$ is Phe, Leu or Tyr;
I$_1$ is Ala or Pro;
J$_1$ is Ile, Val, Ala or Leu;
K$_1$ is Ser, Pro, Leu, Ile or Thr;
L$_1$ is Ser, Pro or Thr;
M$_1$ is Asn, Asp, or Gln;
X and Y are independently selected amino acid residues having side chains which are chemically bonded to each other to form an intramolecular linkage.

The C-terminal portion can be amino, alkylamino, dialkylamino, cycloalkylamino, arylamino, aralkylamino, alkyloxy, aryloxy, aralkyloxy or carboxyl. Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

An additional aspect, compositions and methods of use provided herein are directed to agonist analogues of SEQ ID NO:3 which are not bridged, and wherein X and Y are independently selected from Ala, Ser, Cys, Val, Leu and Ile or alkyl, aryl, or aralkyl esters and ethers of Ser or Cys.

Exemplary compounds include, but are not limited to des-$^1$Lys-h-amylin (SEQ ID NO:4), $^{28}$Pro-h-amylin (SEQ ID NO:5), $^{25,28,29}$Pro-h-amylin (SEQ ID NO:6) $^{18}$Arg$^{25,28}$Pro-h-amylin (SEQ ID NO:7), and des-$^1$Lys$^{18}$Arg$^{25,28}$Pro-h-amylin (SEQ ID NO:8), which all show amylin activity in vivo in treated test animals, (e.g., provoking marked hyperlactemia followed by hyperglycemia). In addition to having activities characteristic of amylin, certain of the compounds provided herein have also been found to possess more desirable solubility and stability characteristics when compared to human amylin. Examples of these compounds include $^{25}$Pro$^{26}$Val$^{28,29}$Pro-h-amylin (SEQ ID NO:9), $^{25,28,29}$Pro-h-amylin (SEQ ID NO: 6), and $^{18}$Arg$^{25,28}$Pro-h-amylin (SEQ ID NO: 7).

Other compounds include $^{18}$Arg$^{25,28,29}$Pro-h-amylin (SEQ ID NO:10), des-$^1$Lys$^{18}$Arg$^{25,28,29}$Pro-h-amylin (SEQ ID NO:11), des-$^1$Lys$^{25,28,29}$Pro-h-amylin (SEQ ID NO:12), $^{25}$Pro$^{26}$Val$^{28,29}$Pro-h-amylin (SEQ ID NO:13), $^{23}$Leu$^{25}$Pro$^{26}$Val$^{28,29}$Pro-h-amylin (SEQ ID NO:14), $^{23}$Leu$^{25}$Pro$^{26}$Val$^{28}$Pro-h-amylin (SEQ ID NO:15), des-$^1$Lys$^{23}$Leu$^{25}$Pro$^{26}$Val$^{28}$Pro-h-amylin (SEQ ID NO:16), $^{18}$Arg$^{23}$Leu$^{25}$Pro$^{26}$Val$^{28}$Pro-h-amylin (SEQ ID NO:17), $^{18}$Arg$^{23}$Leu$^{25,28,29}$Pro-h-amylin (SEQ ID NO:18), $^{18}$Arg$^{23}$Leu$^{25,28}$Pro-h-amylin (SEQ ID NO:19), $^{17}$Ile$^{23}$Leu$^{25,28,29}$Pro-h-amylin (SEQ ID NO:20), $^{17}$Ile$^{25,28,29}$Pro-h-amylin (SEQ ID NO:21), des-$^1$Lys$^{17}$Ile$^{25,28,29}$Pro-h-amylin (SEQ ID NO:22), $^{17}$Ile$^{18}$Arg$^{23}$Leu-h-amylin (SEQ ID NO:23), $^{17}$Ile$^{18}$Arg$^{23}$Leu$^{26}$Val$^{29}$Pro-h-amylin (SEQ ID NO:24), $^{17}$Ile$^{18}$Arg$^{23}$Leu$^{25}$Pro$^{26}$Val$^{28,29}$Pro-h-amylin (SEQ ID NO:25), $^{13}$Thr$^{21}$His$^{23}$Leu$^{26}$Ala$^{28}$Leu$^{29}$Pro$^{31}$Asp-h-amylin (SEQ ID NO:26), $^{13}$Thr$^{21}$His$^{23}$Leu$^{26}$Ala$^{29}$Pro$^{31}$Asp-h-amylin (SEQ ID NO:27), des-$^1$Lys$^{13}$Thr$^{21}$His$^{23}$Leu$^{26}$Ala$^{28}$Pro$^{31}$Asp-h-amylin (SEQ ID NO:28), $^{13}$Thr$^{18}$Arg$^{21}$His$^{23}$Leu$^{26}$Ala$^{29}$Pro$^{31}$Asp-h-amylin (SEQ ID NO:29), $^{13}$Thr$^{18}$Arg$^{21}$His$^{23}$Leu$^{28,29}$Pro$^{31}$Asp-h-amylin (SEQ ID NO:30), and $^{13}$Thr$^{18}$Arg$^{21}$His$^{23}$Leu$^{25}$Pro$^{26}$Ala$^{28,29}$Pro$^{31}$Asp-h-amylin (SEQ ID NO:31).

Amylin agonists contemplated in the use in the methods disclosed herein include Amylin Family Polypeptide-6 (AFP-6) analogs as described in U.S. Provisional Application No. 60/617,468 and PCT Application No. PCT/US05/036456, which are herein incorporated by reference in their entirety. A mature AFP-6 peptide, also known as intermedin, has the following amino acid sequence TQAQLLRVGCVLGTC-QVQNLSHRLWQLMGPAGRQDSAPVDPSSPHSY (SEQ ID NO:32). The AFP-6 or AFP-6 analogs may or may not be amidated at the C-terminal end. Such AFP-6 analogs include those having formula II: $X_1$-$X_2$-$X_3$-$X_4$-$X_5$-$X_6$-$X_7$-$X_8$-QVQNLSHRLWQL-$X_{21}$-$X_{22}$-$X_{23}$-$X_{24}$-$X_{25}$-$X_{26}$-$X_{27}$-$X_{28}$-SAPV-$X_{33}$-PSSPHSY (SEQ ID NO:33) wherein $X_1$ is absent, TQAQLLRVG (SEQ ID NO:34), any of one or more consecutive amino acids of SEQ ID NO:34, N-aryl, or N-acyl with a substituent selected from a C1-C18 alkyl, a substituted alkyl or a heteroaryl moiety;

$X_2$ is M, S, C, substituted L, K, D, or E, where the side chain can be linked via an amide bond, or any amino acid that can form a bond with $X_8$, for example a disulfide or an amide bond;

$X_3$ is V, D, L, G, N, A, or S;

$X_4$ is V, D, L, G, N, A, S or T;

$X_5$ is V, D, L, G, N, A, or S;

$X_6$ is V, D, L, G, N, A, S, or absent;

$X_7$ is T, S, Hse (homoSER), Ahb ((S)-2-Amino-3-hydroxy-3-methylbutanoic acid) or (Ahp) (2R,3R)-2-Amino-3-hydroxy-4-methylpentanoic acid;

$X_8$ is M, S, C, substituted L, K, D, or E, or any amino acid that can form a bond with $X_2$, for example a disulfide or an amide bond;

$X_{21}$ is M, G, P, A, or absent;

$X_{22}$ is M, G, P, A, or absent;

$X_{23}$ is M, G, P, A, or absent;

$X_{24}$ is M, G, P, A, or absent;

$X_{25}$ is M, G, P, A, or absent;

$X_{26}$ is R or absent, wherein when $X_{26}$ is absent, $X_{27}$ is absent;

$X_{27}$ is Q or absent, wherein when $X_{27}$ is absent, $X_{26}$ is absent;

$X_{28}$ is D or E;

$X_{33}$ is D or E; and biologically active fragments thereof.

In other embodiments, AFP-6 analogs comprise, or the active region consists of, compounds having an amino acid sequence of formula (III): $X_1$-$X_2$-QNLSHRLWQL-$X_{13}$-$X_{14}$-$X_{15}$-$X_{16}$-$X_{17}$-$X_{18}$-$X_{19}$-$X_{20}$-SAPV-$X_{25}$-PSSPHSY (SEQ ID NO:35) wherein $X_1$ is Q or absent;

$X_2$ is V or absent;

$X_{13}$ is M, G, P, A, or absent;

$X_{14}$ is M, G, P, A, or absent $X_{15}$ is M, G, P, A, or absent;

$X_{16}$ is M, G, P, A, or absent;

$X_{17}$ is M, G, P, A, or absent, $X_{18}$ is R or absent, wherein when $X_{18}$ is absent, $X_{19}$ is absent;

$X_{19}$ is Q or absent, wherein when $X_{19}$ is absent, $X_{18}$ is absent $X_{20}$ is D or E;

$X_{25}$ is D or E; and biologically active fragments thereof.

Amino acid sequences of exemplary AFP-6 analogs for use in the disclosed methods include:

```
                                              (SEQ ID NO:36)
RVGCVLGTCQVQNLSHRLWQLMGPAGRQDSAPVDPSSPHSY (SEQ ID NO:37)
GCVLGTCQVQNLSHRLWQLMGPAGRQDSAPVDPSSPHSY (SEQ ID NO:38)
CVLGTCQVQNLSHRLWQLMGPAGRQDSAPVDPSSPHSY (SEQ ID NO:39)
QVQNLSHRLWQLMGPAGRQDSAPVDPSSPHSY (SEQ ID NO:40)
VQNLSHRLWQLMGPAGRQDSAPVDPSSPHSY (SEQ ID NO:41)
VQNLSHRL-QLMGPAGRQDSAPVDPSSPHSY (SEQ ID NO:42)
TQAQLLRVGCVLGTCQVQNLSHRLWQLRQDSAPVDPSSPHSY (SEQ ID NO:43)
TQAQLLRVGCVLGTCQVQNLSHRLWQLDSAPVDPSSPHSY (SEQ ID NO:44)
VGCVLGTCQVQNLSHRLWQLRQDSAPVDPSSPHSY (SEQ ID NO:45)
CVLGTCQVQNLSHRLWQLRQESAPVEPSSPHSY (SEQ ID NO:46)
TQAQLLRVGCSNLSTCQVQNLSHRLWQLMGPAGRQDSAPVDPSSPHSY (SEQ ID NO:47)
TQAQLLRVGCNTATCQVQNLSHRLWQLMGPAGRQDSAPVDPSSPHSY (SEQ ID NO:48)
RVGCGNLSTCQVQNLSHRLWQLMGPAGRQDSAPVDPSSPHSY (SEQ ID NO:49)
TQAQLLRVGCDTATCQVQNLSHRLWQLMGPAGRQDSAPVDPSSPHSY (SEQ ID NO:50)
TQAQLLRVGCGNLSTCQVQNLSHRLWQLMGPAGRQDSAPVDPSSPHSY
```

-continued

TQAQLLRVGMVLGTMQVQNLSHRLWQLMGPAGRQDSAPVDPSSPHSY (SEQ ID NO:51)

GMVLGTMQVQNLSHRIWQLMGPAGRQDSAPVDPSSPHSY (SEQ ID NO:52)

VGMVLGTMQVQNLSHRLWQLRQDSAPVDPSSPHSY (SEQ ID NO:53)

RVGCGNLSTCQVQNLSHRLWQLMGPAGRQDSAPVDPSSPHSY (SEQ ID NO:54)

VGCGNLSTCQVQNLSHRLWQLRQDSAPVDPSSPHSY (SEQ ID NO:55)

V-CNTA-TCQVQNLSHRLWQLRQDSAPVDPSSPHSY (SEQ ID NO:56)

GCNTATCQVQNLSHRLWQLRQDSAPVDPSSPHSY (SEQ ID NO:57)

TQAQLLRVGCVLGTCQVQNLSHRLWQLMGPAGRQESAPVEPSSPHSY (SEQ ID NO:58)

TQAQLLRVGCVLGTCQVQNLSHRLWQLMGPAGRQDSAPVEPSSPHSY (SEQ ID NO:59)

GTMQVQNLSHRLWQLRQDSAPVEPSSPHSY (SEQ ID NO:60)

VGCVLGTCQVQNLSHRLWQLMGPAGRQDSAPVEPSSPHSY (SEQ ID NO:61)

VGCVLGTCQVQNLSHRLWQLRQDSAPVEPSSPHSY (SEQ ID NO:62)

GCNTATCQVQNLSHRLWQLRQDSAPVEPSSPHSY (SEQ ID NO:63)

GCSNLSTCQVQNLSHRLWQLRQDSAPVEPSSPHSY (SEQ ID NO:64)

GCGNLSTCQVQNLSHRLWQLRQDSAPVEPSSPHSY (SEQ ID NO:65)

GCVLGTCQVQNLSHRLWQLRQESAPVEPSSPHSY. (SEQ ID NO:66)

Amylin agonists contemplated in the use in the methods disclosed herein include analogs identified in U.S. Pat. No. 6,087,334, the contents of which is hereby incorporated by reference. Such useful amylin agonists include analogs of formula IV: $X_1$-$Xaa_1$-$X_2$-$Xaa_2$-$X_3$-$Xaa_3$-$X_4$-$Xaa_4$-$X_5$-$Xaa_5$-$X_6$ (SEQ ID NO:67) wherein $X_1$ is Lys, Arg or absent;

$X_2$ is $Xaa_6Xaa_7Xaa_8Xaa_9$ (SEQ. ID. NO. 68) or Z-$Xaa_{10}$SerThr, provided that if $X_2$ is Z-$Xaa_{10}$SerThr, then $X_1$ and $Xaa_1$ are both absent;

$X_3$ is AlaThr, AlaSer, SerMet, GluThr or ValThr;

$X_4$ is ArgLeuAla, HisLeuAla, ArgIleAla, LysIleAla, ArgMetAla, HisMetAla, LysMetAla or ArgLeuThr;

$X_5$ is PheLeu, PheIle, PheMet, TyrLeu, TyrIle, TyrMet, TrpIle or TrpMet;

$X_6$ is ArgSerSerGlyTyr (SEQ ID NO:69), LysSerSerGlyTyr (SEQ ID NO:70), HisSerSerGlyTyr (SEQ ID NO:71), ProSerSerGlyTyr (SEQ ID NO:72), ArgSerArgGlyTyr (SEQ ID NO:73), ArgThrSerGlyTyr (SEQ ID NO:74), ArgAlaSerGlyTyr (SEQ ID NO:75), AlaSerSerGlyTyr (SEQ ID NO:76), ArgSerAlaGlyTyr (SEQ ID NO:77), HisSerAlaGlyTyr (SEQ ID NO:78), ArgSerGlyTyr (SEQ ID NO:79), ArgSer, LysSer, HisSer, ArgThr, ProSer or Arg;

$Xaa_1$ is Cys or absent;

$Xaa_2$ is Cys or Ala;

$Xaa_3$ is Gln, Ala or Asn;

$Xaa_4$ is Asn, Ala or Gln;

$Xaa_5$ is Val, Ala, Ile, Met, Leu, PentylGly, or t-butylGly;

$Xaa_6$ is Asn, Gln or Asp;

$Xaa_7$ is Thr, Ser, Met, Val, Leu or Ile;

$Xaa_8$ is Ala or Val;

$Xaa_9$ is Thr or Ser;

$Xaa_{10}$ is Leu, Val, Met or Ile;

Z is an alkanoyl group of about 1 to about 8 carbon atoms or absent;

and pharmaceutically acceptable salts thereof.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

Amylin agonists contemplated in the use in the methods disclosed herein include the amylin family peptides and analogs described in PCT Application No. PCT/US2005/004631, which is herein incorporated by reference in its entirety. Such useful amylin agonists may include analogs comprising an amino acid sequence of formula V: $Xaa_1$ X $Xaa_3$ $Xaa_4$ $Xaa_5$ $Xaa_6$ Y $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$ $Xaa_{29}$ $Xaa_{30}$ $Xaa_{31}$ $Xaa_{32}$ (SEQ ID NO: 80) wherein $Xaa_1$ is A, C, hC (homoCys), D, E, F, I, L, K, hK (homoLys), R, hR (homoArg), S, Hse (homoSer), T, G, Q, N, M, Y, W, P, Hyp (hydroxyPro), H, V or absent;

$Xaa_3$ is A, D, E, N, Q, G, V, R, K, hK, hR, H, I, L, M, or absent;

$Xaa_4$ is A, I, L, S, Hse, T, V, M, or absent;

$Xaa_5$ is A, S, T, Hse, Y, V, I, L, or M;

$Xaa_6$ is T, A, S, Hse, Y, V, I, L, or M;

$Xaa_8$ is A, V, I, L, F, or M;

$Xaa_9$ is L, T, S, Hse, V, I, or M;

$Xaa_{10}$ is G, H, Q, K, R, N, hK, or hR;

$Xaa_{11}$ is K, R, Q, N, hK, hR, or H;

$Xaa_{12}$ is L, I, V, F, M, W, or Y;

$Xaa_{13}$ is A, F, Y, N, Q, S, Hse, or T;

$Xaa_{14}$ is A, D, E, G, N, K, Q, R, H, hR, or hK;

$Xaa_{15}$ is A, D, E, F, L, S, Y, I, V, or M;

$Xaa_{16}$ is L, F, M, V, Y, or I;

$Xaa_{17}$ is H, Q, N, S, Hse, T, or V;

$Xaa_{18}$ is K, hK, R, hR, H, u (Cit), or n (Orn);

$Xaa_{19}$ is F, L, S, Hse, V, I, T, or absent;

$Xaa_{20}$ is H, R, K, hR, hK, N, Q, or absent;

$Xaa_{21}$ is T, S, Hse, V, I, L, Q, N, or absent;

$Xaa_{22}$ is F, L, M, V, Y, or I;

$Xaa_{23}$ is P or Hyp;

$Xaa_{24}$ is P, Hyp, R, K, hR, hK, or H;

$Xaa_{25}$ is T, S, Hse, V, I, L, F, or Y;

$Xaa_{26}$ is N, Q, D, or E;

$Xaa_{27}$ is T, V, S, F, I, or L;

$Xaa_{28}$ is G or A;

$Xaa_{29}$ is S, Hse, T, V, I, L, or Y;

$Xaa_{30}$ is E, G, K, N, D, R, hR, hK, H, or Q;

$Xaa_{31}$ is A, T, S, Hse, V, I, L, F, or Y; and $Xaa_{32}$ is F, P, Y, Hse, S, T, or Hyp;

wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond.

Alkyl chains may include lower alkyl groups having from about 1 to about 6 carbon atoms. In certain embodiments, the intramolecular linkage may be a disulfide, amide, imine, amine, alkyl or alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

Useful amylin agonists may also include analogs comprising the amino acid sequence of formula VI: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{24}$ T N $Xaa_{27}$ G S $Xaa_{30}$ $Xaa_{31}$ $Xaa_{32}$ (SEQ ID NO:81) wherein
  $Xaa_1$ is A, C, D, F, I, K, S, T, or absent;
  $Xaa_2$ is C, D, S, or absent;
  $Xaa_3$ is A, D, N, or absent;
  $Xaa_4$ is A, L, T, or absent;
  $Xaa_5$ is A or S;
  $Xaa_6$ is T, A, S, or V;
  $Xaa_7$ is C, K, or A;
  $Xaa_8$ is A, V, L, or M;
  $Xaa_9$ is L or T;
  $Xaa_{10}$ is G, H, or Q;
  $Xaa_{11}$ is K, R, Q, or hArg;
  $Xaa_{12}$ is L, W, or Y;
  $Xaa_{13}$ is A, F, N, Q, S, or T;
  $Xaa_{14}$ is A, D, E, G, N, K, Q, or R;
  $Xaa_{15}$ is A, D, E, F, L, S, or Y;
  $Xaa_{16}$ is L, or F;
  $Xaa_{17}$ is H, Q, S, or V;
  $Xaa_{18}$ is K, R, hArg, u (Cit), or n (Orn);
  $Xaa_{19}$ is F, L, S, or absent;
  $Xaa_{20}$ is H, Q, or absent;
  $Xaa_{21}$ is T, N, or absent;
  $Xaa_{22}$ is F, L, M, V, or Y;
  $Xaa_{24}$ is P or R;
  $Xaa_{27}$ is T or V;
  $Xaa_{30}$ is E, G, K, or N;
  $Xaa_{31}$ is A or T; and
  $Xaa_{32}$ is F, P, or Y.

Useful amylin agonists may also include analogs comprising the amino acid sequence of formula VII: $Xaa_1$ $Xaa_2$ $Xaa_3$ $Xaa_4$ $Xaa_5$ T $Xaa_7$ $Xaa_8$ $Xaa_9$ $Xaa_{10}$ $Xaa_{11}$ L $Xaa_{13}$ $Xaa_{14}$ $Xaa_{15}$ L $Xaa_{17}$ $Xaa_{18}$ $Xaa_{19}$ $Xaa_{20}$ $Xaa_{21}$ $Xaa_{22}$ P $Xaa_{24}$ T N $Xaa_{27}$ G S $Xaa_{30}$ $Xaa_{31}$ $Xaa_{32}$, (SEQ ID NO:82) wherein
  $Xaa_1$ is A, C, F, I, K, S, or absent;
  $Xaa_2$ is C, D, or S;
  $Xaa_3$ is A, D or N;
  $Xaa_4$ is A, L or T;
  $Xaa_5$ is A or S;
  $Xaa_7$ is C or K;
  $Xaa_8$ is A or V;
  $Xaa_9$ is L or T;
  $Xaa_{10}$ is G, H, or Q;
  $Xaa_{11}$ is K, R, or hArg;
  $Xaa_{13}$ is A, F, N, S, or T;
  $Xaa_{14}$ is A, D, E, G, N, Q, or R;
  $Xaa_{15}$ is A, E, F, L, S, or Y;
  $Xaa_{17}$ is H, S, or V;
  $Xaa_{18}$ is K, R, hArg, u (Cit), or n (Orn);
  $Xaa_{19}$ is F, L, or S;
  $Xaa_{20}$ is H or Q;
  $Xaa_{21}$ is T or N;
  $Xaa_{22}$ is F, L, M, V, or Y;
  $Xaa_{24}$ is P or R;
  $Xaa_{27}$ is T, or V;
  $Xaa_{30}$ is E, G, K, or N;
  $Xaa_{31}$ is A, or T; and
  $Xaa_{32}$ is F, P, or Y.

Useful amylin agonists may also include analogs comprising the ammo acid sequence of formula VIII: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ P $Xaa_{24}$ T N $Xaa_{27}$ G S $Xaa_{30}$ $Xaa_{31}$ $Xaa_{32}$ (SEQ ID NO: 83) wherein
  $Xaa_1$ is A, C, D, F, K, T, or absent;
  $Xaa_2$ is A, C, D, S, or absent;
  $Xaa_3$ is A, D, N, or absent;
  $Xaa_4$ is A, L, T, or absent;
  $Xaa_5$ is A or S;
  $Xaa_6$ is A, S, T, or V;
  $Xaa_7$ is A, C, or K;
  $Xaa_8$ is A, L, M, or V;
  $Xaa_9$ is L or T;
  $Xaa_{10}$ is G, H, or Q;
  $Xaa_{11}$ is K, Q, or R;
  $Xaa_{12}$ is L, W, or Y;
  $Xaa_{13}$ is A, N, Q, S, or T;
  $Xaa_{14}$ is A, D, E, G, K, N, Q, or R;
  $Xaa_{15}$ is A, D, E, F, L, S, or Y;
  $Xaa_{16}$ is F or L;
  $Xaa_{17}$ is H, Q, S or V;
  $Xaa_{18}$ is K, or R;
  $Xaa_{19}$ is F, L, S, or absent;
  $Xaa_{20}$ is H, K, Q, or absent;
  $Xaa_{21}$ is Q, T, or absent;
  $Xaa_{22}$ is F, L, or Y;
  $Xaa_{24}$ is P or R;
  $Xaa_{27}$ is T or V;
  $Xaa_{30}$ is E, K or N;
  $Xaa_{31}$ is A or T; and
  $Xaa_{32}$ is F, Y, or absent.

In a general aspect, the sequence of formula V, VI, VII, or VIII further comprises 1, 2, 3, 4, 5, 6, 7, 8, 9, 10, 11, 12, or more modifications of substitutions, insertions, deletions, elongations and/or derivatizations. In certain embodiments, the sequence of formula V, VI, VII, or VIII comprises a deletion at position 24. In certain embodiments, the sequence of formula V, VI, or VII comprises a Val inserted between amino acids at positions 22 and 23. In other embodiments, the sequence of formula V, VI, or VII comprises a Gln inserted between positions 22 and 23. In still other embodiments, the sequence of formula V, VI, or VII comprises a sequence of Gln-Thr-Tyr between positions 22 and 23. In yet other embodiments, the sequence of formula V, VI, or VII comprises a sequence of Leu-Gln-Thr-Tyr (SEQ ID NO: 84) between positions 22 and 23. In another general aspect, the modifications of formula V, VI, or VII may be at the N-terminal end. In certain embodiments, the N-terminal portion of formula V, VI, or VII has an added octylglycine. In other embodiments, the N-terminal portion of formula V, VI, or VII has an added isocap. Other embodiments are described in PCT Application No. PCT/US2005/004631 and incorporated by reference.

Exemplary compounds described with reference to human amylin (SEQ ID NO: 1; hAmylin), rat amylin (SEQ ID NO:2; rAmylin), and salmon calcitonin (sCT) CSNLSTCV-LGKLSQELHKLQTYPRTNTGSGTP (SEQ ID NO:85) with modifications at the position(s) indicated include, (1-7 hAmylin)($^{18}$Arg 8-27)(33-37 hAmylin) (SEQ ID NO:86);

(1-7 hAmylin)($^{11,18}$Arg$^{22}$Leu 8-27sCT)(33-37 hAmylin) (SEQ ID NO:87);

(1-7 hAmylin)($^{11,18}$Arg$^{24}$Pro 8-27 sCT)(33-37 hAmylin) (SEQ ID NO:88);

(1-7 hAmylin)($^{11,18}$Arg 8-24 sCT)(30-37 hAmylin) (SEQ ID NO:89);

(1-7 hAmylin)($^{11,18}$Arg 8-21 sCT)(27-37 rAmylin) (SEQ ID NO:90);

($^{8}$Val$^{9}$Leu$^{10}$Gly 1-15 hAmylin($^{18}$Arg 16-27)(30-37 hAmylin) (SEQ ID NO:91);

($^{1}$Ala 1-7 hAmylin)($^{11,18}$Arg 8-27 sCT)(33-37 hAmylin) (SEQ ID NO:92);

($^{3}$Ala 1-7 hAmylin)($^{11,18}$Arg 8-27 sCT)(33-37 hAmylin) (SEQ ID NO:93);

($^{4}$Ala 1-7 hAmylin)($^{11,18}$Arg 8-27 sCT)(33-37 hAmylin) (SEQ ID NO:94);

($^{6}$Ala 1-7 hAmylin)($^{11,18}$Arg 8-27 sCT)(33-37 hAmylin) (SEQ ID NO:95);

($^{2}$Ala$^{11,18}$Arg 1-27 sCT)(33-37 hAmylin) (SEQ ID NO:96);

(Isocap-$^{7}$Ala$^{11,18}$Arg 5-27 sCT)(33-37 hAmylin) (SEQ ID NO:97);

($^{4}$Ala$^{11,18}$Arg 1-27 sCT)(33-37 hAmylin) (SEQ ID NO:98);

($^{5}$Ala$^{11,18}$Arg 1-27 sCT)(33-37 hAmylin) (SEQ ID NO:99);

($^{6}$Ala$^{11,18}$Arg 1-27 sCT)(33-37 hAmylin) (SEQ ID NO:100);

(1-7 hAmylin)($^{11}$Arg 8-27 sCT)(33-37 hAmylin) (SEQ ID NO:101);

($^{13}$Ser$^{14}$Gln$^{15}$Glu 1-16 hAmylin)($^{17}$Arg$^{30}$Asn$^{32}$Tyr 17-32 sCT) (SEQ ID NO:102);

($^{3}$Ala$^{11,18}$Arg 1-27 sCT)(33-37 hAmylin) (SEQ ID NO:103);

(Acetyl-$^{2,7}$Agy$^{11,18}$Arg 1-27 sCT)(33-37 hAmylin) (SEQ ID NO:104);

(Acetyl-$^{2,7}$Agy 1-7 hAmylin)($^{11,18}$Arg 8-27 sCT)(33-37 hAmylin) (SEQ ID NO:105);

(Isocap-$^{7}$Ala$^{10}$Aib$^{11}$Lys(For)$^{17}$Aib$^{18}$Lys(For) 5-27 sCT)(33-37 hAmylin) (SEQ ID NO:106);

(Isocap-$^{7}$Ala$^{10}$Aib$^{11}$Lys(For)$^{17}$Aib$^{18}$Lys(For) 5-24sCT)(30-37 hAmylin) (SEQ ID NO:107);

(Isocap-$^{7}$Ala$^{10}$Aib$^{11}$Lys(For)$^{17}$Aib$^{18}$Lys(For) 5-22 sCT)($^{28,29}$Pro 28-37 hAmylin) (SEQ ID NO:108);

(Isocap-$^{7}$Ala$^{10}$Aib$^{11}$Lys(For)$^{17}$Aib$^{18}$Lys(For) 5-21 sCT)(28,29Pro 27-37 hAmylin) (SEQ ID NO: 109);

(1-7 hAmylin)(LLQQWQKLLQKLKQ (SEQ ID NO: 110))($^{28}$Pro$^{29}$Arg$^{32}$Thr 27-37 hAmylin) (SEQ ID NO:111);

(1-7 hAmylin)(LLQQLQKLLQKLKQY (SEQ ID NO:112))($^{28}$Pro$^{29}$Arg$^{32}$Thr 28-37 hAmylin) (SEQ ID NO:113);

($^{6}$Ser 1-7 hAmylin)($^{11,18}$Arg 8-27 sCT)(33-37 hAmylin) (SEQ ID NO: 114);

($^{6}$Val 1-7 hAmylin)($^{11,18}$Arg 8-27 sCT)(33-37 hAmylin) (SEQ ID NO:115);

(1-7 hAmylin)($^{11,18}$Arg 8-18 sCT)($^{28}$Pro$^{29}$Arg$^{32}$Thr 27-37 hAmylin) (SEQ ID NO:116);

(1-7 hAmylin)($^{11}$Arg 8-17 sCT)($^{28}$Pro$^{29}$Arg$^{32}$Thr 27-37 hAmylin) (SEQ ID NO:117);

(1-7 hAmylin)($^{11}$Arg 8-16 sCT)($^{27}$Tyr$^{28}$Pro$^{29}$Arg$^{32}$Thr 27-37 hAmylin) (SEQ ID NO:118);

(1-7 hAmylin)($^{11}$Arg 8-15sCT)($^{27}$Tyr$^{28}$Pro$^{21}$Arg$^{32}$Thr 27-37 hAmylin) (SEQ ID NO:119);

(1-7 hAmylin)($^{11}$Arg 8-14 sCT)($^{27}$Tyr$^{28}$Pro$^{29}$Arg$^{32}$Thr 27-37 hAmylin) (SEQ ID NO:120);

(1-7 hAmylin)($^{11,18}$Lys(For) 8-27 sCT)(33-37 h Amylin) (SEQ ID NO:121);

($^{6}$D-Thr 1-7 hAmylin)($^{11,18}$Arg 8-27 sCT)(33-37 hAmylin) (SEQ ID NO:122);

(Acetyl-1-7 hAmylin)($^{11,18}$Lys(PEG5000) 8-27 sCT)(33-37 hAmylin) (SEQ ID NO:123);

(Acetyl-1-7 hAmylin)($^{11}$Lys(PEG5000)$^{18}$Arg 8-27 sCT)(33-37 hAmylin) (SEQ ID NO:124);

(Acetyl-$^{1}$Ala 1-7 hAmylin)($^{11}$Arg$^{18}$Lys(PEG5000) 8-27 sCT)(33-37 hAmylin) (SEQ ID NO:125);

(1-7 hAmylin)($^{11,18}$Arg 8-21 sCT)(19-27 sCT)(33-37 hAmylin) (SEQ ID NO:126);

(1-7 hAmylin)($^{11,18}$Arg 8-21 sCT)($^{18}$Leu 18-27 sCT)(33-37 hAmylin) (SEQ ID NO:127);

(1-7 hAmylin)(8-27 sCT)(33-37 hAmylin) (SEQ ID NO:128);

($^{5}$Ser 1-7 hAmylin)($^{11,18}$Arg 8-27 sCT)(33-37 hAmylin) (SEQ ID NO:129);

(1-12 hAmylin)($^{18}$Arg 13-27 sCT)(33-37 hAmylin) (SEQ ID NO:130);

(1-12 hAmylin)($^{18}$Arg 13-24 sCT)(30-37 hAmylin) (SEQ ID NO:131);

($^{5}$Ser$^{15}$Glu$^{18}$Arg 1-18hAmylin)(19-24 sCT)(30-37 hAmylin) (SEQ ID NO:132;

($^{6}$Hse 1-7 hAmylin)($^{11,18}$Arg 8-27 sCT)(33-37 hAmylin) (SEQ ID NO:133);

($^{6}$Ahb 1-7 hAmylin)($^{11,18}$Arg 8-27 sCT)(33-37 hAmylin) (SEQ ID NO:134);

($^{6}$Ahp 1-7hAmylin)($^{11,18}$Arg 8-27 sCT)(33-37 hAmylin) (SEQ ID NO:135);

$^{6}$Thr(OPO$_{3}$H$_{2}$) 1-7 hAmylin)($^{11,18}$Arg 8-27 sCT)(33-37 hAmylin) (SEQ ID NO:136);

($^{7}$Ala$^{11,18}$Arg 5-27 sCT)(33-37 hAmylin) (SEQ ID NO:137);

(1-7 hAmylin)($^{11,18}$Orn 8-27 sCT)(33-37 hAmylin) (SEQ ID NO:138);

(1-7 hAmylin)($^{11,18}$Cit 8-27 sCT)(33-37 hAmylin) (SEQ ID NO:139);

(1-7 hAmylin)($^{11,18}$homoLys 8-27 sCT)(33-37 hAmylin) (SEQ ID NO:140);

(L-Octylglycine-1-7hAmylin)($^{11,18}$Arg 8-27 sCT)(33-37 hAmylin) (SEQ ID NO:141);

(N-3,6-dioxaoctanoyl-1-7-hAmylin)($^{11,18}$Arg 8-27 sCT)(33-37 hAmylin) (SEQ ID NO:142);

(cyclo(1-7)-$^{1}$Asp$^{7}$Lys$^{11,18}$Arg 1-27 sCT)(33-37 hAmylin) (SEQ ID NO:143);

(cyclo(2-7)-²Asp⁷Lys 1-7 hAmylin)(¹¹,¹⁸Arg 8-27 sCT)(33-37 hAmylin) (SEQ ID NO:144);

(cyclo (2-7) hAmylin)(¹¹,¹⁸Arg 8-27 sCT)(33-37 hAmylin) (SEQ ID NO:145);

(1-7 hAmylin)(¹¹,¹⁸Arg 8-27 sCT)(33-37 hAmylin-9Anc) (SEQ ID NO:146);

(1-7 hAmylin)(¹¹,¹⁸Arg 8-27 sCT)(33-37 hAmylin-L-octylglycine) (SEQ ID NO:147);

(N-isocaproyl-1-7-hAmylin)(¹¹,¹⁸Arg 8-27sCT)(33-37 hAmylin) (SEQ ID NO:148);

(1-7 hAmylin)(¹¹,¹⁸homoArg 8-27 sCT)(33-37 hAmylin) (SEQ ID NO:149);

(¹Phe 1-7 hAmylin)(¹¹,¹⁸Arg 8-27 sCT)(33-37 hAmylin) (SEQ ID NO:150);

(1-7 hAmylin)(¹¹,¹⁸Arg 8-24 sCT)(³²Thr 30-37 hAmylin) (SEQ ID NO:151);

(1-7 hAmylin)(¹¹,¹⁸Arg 8-27 sCt)(33-37 hAmylin) (SEQ ID NO:152);

(¹⁵Glu¹⁸Arg 1-18 hAmylin)(19-24 sCT)(30-37 hAmylin) (SEQ ID NO:153);

(¹³Ala¹⁴Asp¹⁵Phe 1-18 hAmylin)(19-23 sCT)(30-37 hAmylin) (SEQ ID NO:154); and (2-18 hAmylin)(19-23 sCT)(30-36 hAmylin) (SEQ ID NO:155). Peptides useful in the compositions and methods provided herein, like those above, can be in the acid or amide form.

Exemplary peptides also for use in the compositions and methods provided herein include:

```
                                              (SEQ ID NO:156)
KCNTATCVLGKLSQELHRLQTYPRTNTGSNTY (SEQ ID NO:157)
KCNTATCVLGRLSQELHRLQTLPRTNTGSNTY (SEQ ID NO:158)
KCNTATCVLGRLSQELHRLQTYPPTNTGSNTY (SEQ ID NO:159)
KCNTATCVLGRLSQELHRLQTYPRTNVGSNTY (SEQ ID NO:160)
KCNTATCVLGRLSQELHRLQTLPPTNVGSNTY (SEQ ID NO:161)
KCNTATCVLGRLANFLHRLQTYPRTNTGSNTY (SEQ ID NO:162)
ACNTATCVLGRLSQELHRLQTYPRTNTGSNTY (SEQ ID NO:163)
KCNAATCVLGRLSQELHRLQTYPRTNTGSNTY (SEQ ID NO:164)
KCNTAACVLGRLSQELHRLQTYPRTNTGSNTY (SEQ ID NO:165)
CANLSTCVLGRLSQELHRLQTYPRTNTGSNTY (SEQ ID NO:166)
isocaproyl-STAVLGRLSQELHRLQTYPRTNTGSNTY (SEQ ID NO:167)
CSNASTCVLGRLSQELHRLQTYPRTNTGSNTY (SEQ ID NO:168)
GSNLATCVLGRLSQELHRLQTYPRTNTGSNTY (SEQ ID NO:169)
CSNLSACVLGRLSQELHRLQTYPRTNTGSNTY (SEQ ID NO:170)
KCNTATCVLGRLSQELHKLQTYPRTNTGSNTY (SEQ ID NO:171)
KCNTATCVLGRLSQELHRLQTYPRTNTGSGTP (SEQ ID NO:172)
CSALSTCVLGRLSQELHRLQTYPRTNTGSNTY (SEQ ID NO:173)
Ac-(Agy)SNLST(Agy)VLGRLSQELHRLQTYPRTNTGSNTY (SEQ ID NO:174)
Ac-K(Agy)NTAT(Agy)VLGRLSQELHRLQTYPRTNTGSNTY (SEQ ID NO:175)
Isocaproyl-STAVL(Aib)RLSQELRLQTYPRTNTGSGTP (SEQ ID NO: 176)
Isocaproyl-STAVLG[K(For)]LSQELH[K(For)]LQTYPRTNTGSGTP (SEQ ID NO:177)
Isocaproyl-STAVL(Aib)[K(For)]LSQEL(Aib)[K(For)]LQTYPRTNTGSNTY (SEQ ID NO:178)
Isocaproyl-STAVL(Aib)[K(For)]LSQEL(Aib)[K(For)]LQTYPRTNVGSNTY (SEQ ID NO:179)
KCNTATCLLQQLQKLLQKLKQYPRTNTGSNTY (SEQ ID NO:180)
KCNTASCVLGRLSQELHRLQTYPRTNTGSNTY (SEQ ID NO:181)
KCNTAVCVLGRLSQELHRLQTYPRTNTGSNTY (SEQ ID NO:182)
KCNTATCVLGRLSQELHRYPRTNTGSNTY (SEQ ID NO:183)
KCNTATCVLG[K(For)]LSQELH[K(For)L]QTYPRTNTGSNTY (SEQ ID NO:184)
KCNTA(d-Thr)CVLGRLSQELHRLQTYPRTNTGSNTY (SEQ ID NO:185)
KCNTA(dAh)CVLGRLSQELHRLQTYPRTNTGSNTY (SEQ ID NO:186)
Ac-ACNTATCVLGRLSQELHK(PEG5000)LQTYPRTNTGSNTY (SEQ ID NO:187)
KCNTATCVLGRLSQELHRLQTLQTYPRTNTGSNTY (SEQ ID NO:188)
KCNTATCVLGRLSQELHRLQTLLQTYPRTNTGSNTY (SEQ ID NO:189)
KCNTATCVLGKLSQELHKLQTYPRTNTGSNTY (SEQ ID NO:190)
KCNTSTCVLGRLSQELHRLQTYPRTNTGSNTY (SEQ ID NO:191)
KCNTATCATQRLSQELHRLQTYPRTNTGSNTY (SEQ ID NO:192)
KCNTATCATQRLSQELHRLQTYPRTNVGSNTY
```

-continued

KCNTSTCATQRLANELVRLQTYPRTNVGSNTY (SEQ ID NO:193)

KCNTA(Hse)CVLGRLSQELHRLQTYPRTNTGSNTY (SEQ ID NO:194)

KCNTA(Ahb)CVLGRLSQELHRLQTYPRTNTGSNTY (SEQ ID NO:195)

KCNTA(Ahp)CVLGRLSQELHRLQTYPRTNTGSNTY (SEQ ID NO:196)

KCNTAT(OPO$_3$H$_2$)CVLGRLSQELHRLQTYPRTNTGSNTY (SEQ ID NO:197)

KCNTATCVLG(Orn)LSQELH(Orn)LQTYPRTNTGSNTY (SEQ ID NO:198)

KCNTATCVLG(Cit)LSQELH(Cit)LQTYPRTNTGSNTY (SEQ ID NO:199)

KCNTATCVLG(hK)LSQELH(hK)LQTYPRTNTGSNTY (SEQ ID NO:200)

L-OctylglycineKCNTATCVLGRLSQELHRLQTYPRTNTGSNTY (SEQ ID NO:201)

N-3,6-dioxaoctanoyl-CNTATCVLGRLSQELHRLQTVPRTNTGSNTY (SEQ ID NO:202)

KCNTATCMLGRYTQDFHRLQTYPRTNTGSNTY (SEQ ID NO:203)

DSNLSTKVLGRLSQELHRLQTYPRTNTGSNTY (SEQ ID NO:204)

KDNTATKVLGRLSQELHRLQTYPRTNTGSNTY (SEQ ID NO:205)

CNTATCVLGRLSQELHRLQTYPRTNTGSNTY (SEQ ID NO:206)

KCNTATCVLGRLSQELHRLQTYPRTNTGSNTY(9Anc) (SEQ ID NO:207)

KCNTATCVLGRLSQELHRLQTYPRTNTGSNTY(L-octylglycine) (SEQ ID NO:208)

N-isocaproyl-KCNTATCVLGRLSQELHRLQTYPRTNTGSNTY (SEQ ID NO:209)

KCNTATCVLG(hR)LSQELH(hR)LQTYPRTNTGSNTY (SEQ ID NO:210)

FCNTATCVLGRLSQELHRLQTYPRTNTGSNTY (SEQ ID NO:211)

KCNTATCVLGRLSQELH(Cit)LQTYPRTNTGSNTY (SEQ ID NO:212)

KCNTATCVLGRLSQELH(Orn)LQTYPRTNTGSNTY (SEQ ID NO:213)

ICNTATCVLGRLSQELHRLQTYPRTNTGSNTY (SEQ ID NO:214)

1-Octylglycine-CNTATCVLGRLSQELHRLQTYPRTNTGSNTY (SEQ ID NO:215)

Isocaproyl-CNTATCVLGRLSQELHRLQTYPRTNTGSNTY (SEQ ID NO:216)

KCNTATCVLG(Cit)LSQELHRLQTYPRTNTGSNTY (SEQ ID NO:217)

KCNTATCVLGRLSQELHRLQTYPRTNTGSNTY(4ABU) (SEQ ID NO:218)

Isocaproyl-KCNTATCVLGRLSQELHRLQTYPRTNTGSNTY(4ABu) (SEQ ID NO:219)

KCNTSTCATQRLANELVRLQTYPRTNVGSEAF (SEQ ID NO:220)

KCNTATCVLGRLSQELHRLQTYPTNVGSEAF (SEQ ID NO:221)

KCNTATCVLGRLSRSLHRLQTYPRTNTGSNTY (SEQ ID NO:222)

KCNTATCVTHRLSQELHRLQTYPRTNTGSNTY (SEQ ID NO:223)

KCNTATCVLGRLADFLHRLQTYPRTNTGSNTY (SEQ ID NO:224)

CNTATCVLGRLSQELHRLQTYPRTNTGSNT (SEQ ID NO:225)

KCNTATCVLGRLSQELHRLQNFVPRTNTGSNTY (SEQ ID NO:226)

KCNTATCVLGRLSQELHRLQTYPRTNTGSETF (SEQ ID NO:227)

ACDTATCVLGRLSQELHRLQTYPRTNTGSNTY (SEQ ID NO:228)

KCNTATCVLGRLSQELHRLQTYPRTNTGSKAF (SEQ ID NO:229)

KCDTATCVTHRLAGLLSRSQTYPRTNTGSNTY (SEQ ID NO:230)

KCNTATCVLGRLADALHRLQTYPRTNTGSNTY (SEQ ID NO:231)

KCNTATCVLGRLAAFLHRLQTYPRTNTGSNTY (SEQ ID NO:232)

SCNTATCVLGRLADFLHRLQTYPRTNTGSNTY (SEQ ID NO:233)

KCNTATCVLGRLSQELHRLQTMPRTNTGSNTY (SEQ ID NO:234)

KCNTATCVLGRLSQELHRLQTVPRTNTGSNTY (SEQ ID NO:235)

KCNTATCVLGRLNEYLHRLQTYPRTNTGSNTY (SEQ ID NO:236)

SCNTATCVLGRLSQELHRLQTYPRTNTGSNTY (SEQ ID NO:237)

KCNTATCVLGRLTEFLHRLQTYPRTNTGSNTY (SEQ ID NO:238)

KCNTATCVLGRLAEFLHRLQTYPRTNTGSNTY (SEQ ID NO:239)

KCNTATCVLGRLTDYLHRLQTYPRTNTGSNTY (SEQ ID NO:240)

KCNTATCVLGRLAQFLHRLQTYPRTNTGSNTY (SEQ ID NO:241)

KCNTATCVLGRLADFLHRFQTFPRTNTGSNTY (SEQ ID NO:242)

KCNTATCVLGRLADFLHRFHTFPRTNTGSNTY (SEQ ID NO:243)

KCNTATCVLGRLADFLHRFQTFPRTNTGSGTP (SEQ ID NO:244)

```
CNTATCVLGRLADFLHRLQTYPRTNTGSNTY    (SEQ ID NO:245)

KCDTATCVLGRLSQELHRLQTYPRTNTGSNTY   (SEQ ID NO:246)

KCNTATCVLGRLFDFLHRLQTYPRTNTGSNTY   (SEQ ID NO:247)

KCNTATCVLGRLAAALHRLQTYPRTNTGSNTY   (SEQ ID NO:248)

TCDTATCVLGRLSQELHRLQTYPRTNTGSNTY   (SEQ ID NO:249)

CSNLSTCATQRLANELVRLQTYPRTNVGSNTY   (SEQ ID NO:250)

KCNTATCATQRLANELVRLQTYPRTNVGSNTY   (SEQ ID NO:251)

CSNLSTCVLGRLSQELHRLQTYPRTNTGSNTY   (SEQ ID NO:252)

KCNTATCVLGRLSQELHRLQTYPRTNTGSNTY.  (SEQ ID NO:253)
```

In some embodiments, compounds comprising the amino acid sequence KCNTATCVLGRLSQELHRLQTYPRTNTGSNTY (SEQ ID NO:253) are of particular use in the disclosed methods.

Derivatives of the agonists and analogs are also included within the methods provided in which the stereochemistry of individual amino acids may be inverted from (L)/S to (D)/R at one or more specific sites. Also included within the methods provided are the agonists and analogs modified by glycosylation of Asn, Ser and/or Thr residues. Compounds useful in the methods provided may also be biologically active fragments of the peptides (native, agonist, analog, and derivative) herein described.

Agonist and analogs of amylin that contain less peptide character are included within the methods provided. Such peptide mimetics may include, for example, one or more of the following substitutions for —CO—NH— amide bonds: depsipeptides (—CO—O—), iminomethylenes (—CH$_2$—NH—), trans-alkenes (—CH=CH—), beta-enaminonitriles (—C(=CH—CN)—NH—), thioamides (—CS—NH—), thiomethylenes (—S—CH2- or —CH2-S—), methylenes (—CH2-C2-) and retro-amides (—NH—CO—).

Compounds for use in the methods provided form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). In certain embodiments, the compounds form acetate, hydrochloride, and trifluoroacetate salts.

Amylin agonists useful in the compositions and methods provided herein may also include fragments of amylin and its analogs as described above as well as those described in EP 289287, the contents of which are herein incorporated by reference. Amylin agonists analogs may also be compounds having at least 60, 65, 70, 75, 80, 85, 90, 95, or 99% amino acid sequence identity to SEQ ID NO:1, or any of the amylin analogs specifically described herein having amylin activity. Amylin agonists also include small chemical molecules and non-peptide molecules, for example those based on small molecule chemistry. In some embodiments, amylin agonists are not small chemical molecules.

"Amylin activity" as used herein may include at least one of the activities known in the art as described below. Amylin activity may also include the ability of amylin to modulate the stress response, affect GC and/or affect CFR activity in a body. Desirable amylin agonists or amylin analogs may have at least one property shared by the antipsychotic, antidepressant, and anxiolytic agents used herein in Examples 2 and 3. Amylin agonist analogs also include insertions, deletions, extensions, truncations, and/or substitutions in at least one or more amino acid positions of SEQ ID NO:1 or any of the amylin analogs specifically described herein. The number of amino acid insertions, deletions, or substitutions may be at least 5, 10, 15, 20, or 25 amino acid insertions, deletions, or substitutions. The number of amino acid insertions, deletions, or substitutions may be not more than 5, 10, 15, 20, 25, or 30 amino acid insertions, deletions, or substitutions. Insertions, extensions, or substitutions may be with other natural amino acids, synthetic amino acids, peptidomimetics, or other chemical compounds. It is contemplated that in certain embodiments, amylin agonists, useful in certain embodiments, may not include calcitonins and/or CGRPs. For example, in certain embodiments, calcitonins and/or CGRPs may be excluded from the scope of amylin agonist in the treatment of mood disorders, anxiety disorders or substance-related disorders. However, calcitonins and/or CGRPs may be included in the scope of amylin agonists for other conditions like sleeping or eating disorders. Similarly, in certain embodiments, amylin agonists, useful in methods provided, may not include calcitonin and/or CGRP analogs.

In general, amylin agonists or amylin agonist analogs are recognized as referring to compounds which, by directly or indirectly interacting or binding with one or more receptors, mimics an action of amylin. They may also be referred to as amylinomimetics.

Activity as amylin agonists and/or analogs can be confirmed and quantified by performing various screening assays, including the nucleus accumbens receptor binding assay, the soleus muscle assay, a gastric emptying assay, or by the ability to induce hypocalcemia or reduce postprandial hyperglycemia in mammals. Methods of testing compounds for amylin activity are known in the art. Exemplary screening methods and assays for testing amylin agonists are described in U.S. Pat. Nos. 5,264,372 and 5,686,411, which are incorporated herein by reference.

The receptor binding assay, a competition assay that measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand, are analyzed by computer using analyses by nonlinear regression to a 4-parameter logistic equation (INPLOT program, GraphPAD Software, San Diego, Calif.) or the ALLFIT program of DeLean et al. (ALL-FIT, Version 2.7 (NIH, Bethesda, Md. 20892)). Munson et al. (1980) *Anal. Biochem.* 107:220-239.

Assays of biological activity of amylin agonists/analogs in the soleus muscle may be performed using previously described methods (Leighton et al. (1988) *Nature* 335:632-635; Cooper et al. (1988) *Proc. Natl. Acad. Sci. USA* 85:7763-7766), in which amylin agonist activity may be assessed by measuring the inhibition of insulin-stimulated glycogen synthesis. In brief, an exemplary method includes soleus muscle strips prepared from 12-h fasted male Wistar rats. The tendons of the muscles are ligated before attachment to stainless steel clips. Muscle strips are pre-incubated in Erlenmeyer flasks containing 3.5 ml Krebs-Ringer bicarbonate buffer, 7 mM N-2-hydroxyethyl-piperazine-N'-2-ethane-sulphonic acid, pH 7.4, and 5.5 mM pyruvate. Flasks are sealed and gassed continuously with $O_2$ and $CO_2$ in the ratio 19:1 (v/v). After pre-incubation of muscles in this medium for 30 min at 37° C. in an oscillating water bath, the muscles strips are transferred to similar vials containing identical medium (except pyruvate) with added [U-$^{14}$C] glucose (0.5 µCi/ml) and insulin (100 µU/ml). The flasks are sealed and re-gassed for an initial 15 min in a 1-h incubation. At the end of the incubation period, muscles are blotted and rapidly frozen in liquid $N_2$. The concentration of lactate in the incubation medium can be determined spectrophotometrically and [U-$^{14}$C] glucose incorporation in glycogen measured.

Methods of measuring the rate of gastric emptying are disclosed in, for example, Young et al. (1995) *Diabetologia* 38:642-648. In a phenol red method, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Amylin agonist compounds may exhibit activity in the receptor binding assay on the order of less than about 1 to 5 nM, in some embodiments less than about 1 nM and in some embodiments less than about 50 pM. In the soleus muscle assay, amylin agonist compounds may show $EC_{50}$ values on the order of less than about 1 to 10 micromolar. In the gastric emptying assays, amylin agonist compounds show $ED_{50}$ values on the order of less than 100 µg/rat.

In one exemplary method of making the compounds, compounds provided herein may be prepared using standard solid-phase peptide synthesis techniques, for example using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein. Other methods of synthesizing or expressing amylin and amylin agonists and purifying them are known to the skilled artisan.

Formulation/Administration/Dosage

The amylin, amylin agonists, amylin analogs, and amylin derivatives (herein referred to in this section as the "compounds") may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang et al. (1988) *Journal of Parenteral Science and Technology Technical Report No.* 10, Supp. 42:2S.

In general, the compounds may be formulated into a stable, safe pharmaceutical composition for administration to a patient. Pharmaceutical formulations contemplated for use in the methods described herein may comprise approximately 0.01 to 6.0% (w/v), or 0.05 to 1.0%, of the compound; approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl-, ethyl-, propyl- and butyl-parabens and phenol. Such a preservative is generally included if the formulated peptide is to be included in a multiple use product.

In a particular embodiment, a pharmaceutical formulation may contain a range of concentrations of the compound, e.g., between about 0.01% to about 98% (w/v), or between about 1 to about 98% (w/v), or between 80% and 90% (w/v), or between about 0.01% to about 50% (w/v), or between about 10% to about 25% (w/v) in this embodiment. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the formulation. An excipient may be included in the presently described formulations at various concentrations. For example, an excipient may be included in the concentration range from about 0.02% to about 20% (w/w), about 0.02% and 0.5% (w/w), about 0.02% to about 10% (w/w), or about 1% to about 20% (w/w). In addition, similar to the present formulations themselves, an excipient may be included in solid (including powdered), liquid, semi-solid or gel form.

As described herein, a variety of liquid vehicles are suitable for use in the present peptide formulations, for example, water or an aqueous/organic solvent mixture or suspension. The pharmaceutical formulations may be composed in various forms, e.g., solid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

The stability of a peptide formulation is enhanced by maintaining the pH of the formulation in the range of about 3.0 to about 7.0 when in liquid form. In one embodiment, the pH of the formulation is maintained in the range of about 3.5 to 5.0, or about 3.5 to 6.5, or about 3.7 to 4.3, or about 3.8 to 4.2. A particular pH may be about 4.0. While not seeking to be bound by this theory, it is presently understood that, in some embodiments, where the pH of the pharmaceutical formulation exceeds 5.5, chemical degradation of the peptide may be accelerated such that the shelf life is less than about two years.

In some embodiments, the buffer used in the practice of the present methods is an acetate buffer (typically at a final formulation concentration of from about 1-5 mM, e.g., 1.5 mM, to about 60 mM), phosphate buffer (typically at a final formulation concentration of from about 1-5 mM, e.g., 1.5 mM, to about 30 mM) or glutamate buffer (typically at a final formulation concentration of from about 1-5 mM, e.g., 1.5 mM, to about 60 mM). In one embodiment, the buffer is acetate at a final formulation concentration of from about 5 mM to about 30 mM.

A stabilizer may be included in the present formulation but, and importantly, is not necessarily needed. If included, however, a stabilizer useful in the practice of the present formulation is a carbohydrate or a polyhydric alcohol. A suitable stabilizer useful in the practice of the present methods is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. In embodiments in which the subjects have diabetes, suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic subjects.

In certain embodiments, if a stabilizer is included, the compound is stabilized with a polyhydric alcohol such as sorbitol, mannitol, inositol, glycerol, xylitol, and polypropylene/ethylene glycol copolymer, as well as various PEGs of molecular weight 200, 400, 1450, 3350, 4000, 6000, and 8000). Mannitol is an example of a particular polyhydric alcohol. Another useful feature of the lyophilized formulations described herein is the maintenance of the tonicity of the lyophilized formulations with the same formulation component that serves to maintain their stability. Mannitol is a particular polyhydric alcohol used for this purpose.

The United States Pharmacopeia (USP) states that anti-microbial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Anti-microbial agents should be evaluated to ensure compatibility with all other components of the formula, and their activity should be evaluated in the total formula to ensure that a particular agent that is effective in one formulation is not ineffective in another. It is not uncommon to find that a particular anti-microbial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), the typical range for each preservative, alone or in combination with others, is: benzyl alcohol (0.1-1.0%), or m-cresol (0.1-0.6%), or phenol (0.1-0.8%) or combination of methyl (0.05-0.25%) and ethyl- or propyl- or butyl-(0.005%-0.03%) parabens. The parabens are lower alkyl esters of para-hydroxybenzoic acid. A detailed description of each preservative is set forth in "Remington's Pharmaceutical Sciences" as well as Pharmaceutical Dosage Forms: Parenteral Medications, Vol. 1, 2nd ed., Avis et al. Ed., Mercel Dekker, New York, N.Y. (1992).

Pramlintide, $^{25,28,29}$Pro-h-amylin, does not have a tendency to adsorb onto the glass in a glass container when in a liquid form, therefore, a surfactant is not required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl)dimethylammonio]1-propanesulfonate), BRIJ® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations typically may be isotonic or substantially isotonic.

A suitable vehicle for parenteral products is water. Water of suitable quality for parenteral administration can be prepared either by distillation or by reverse osmosis. Water for injection is the preferred aqueous vehicle for use in the pharmaceutical injectable formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation provided herein.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Form a Vitrum. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

In order to permit introduction of a needle from a hypodermic syringe into a multiple-dose vial and provide for resealing as soon as the needle is withdrawn, the open end of each vial is typically sealed with a rubber stopper closure held in place by an aluminum band. Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. These stoppers pass the stopper integrity test when tested using patient use patterns, e.g., the stopper can withstand at least about 100 injections. Alternatively, the peptide can be lyophilized in vials, syringes or cartridges for subsequent reconstitution. Liquid formulations provided herein can be filled into one or two chambered cartridges, or one or two chamber syringes.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (for example, preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation provided herein. Typical sterilization processes include filtration, steam (moist heat), dry heat, gases (e.g., ethylene oxide, formaldehyde, chlorine dioxide, propylene oxide, beta-propiolactone, ozone, chloropicrin, peracetic acid methyl bromide and the like), exposure to a radiation source, and aseptic handling. Filtration is an exemplary method of sterilization for liquid formulations described herein. The sterile filtration involves filtration through 0.45 µm and 0.22 µm (1 or 2) which may be connected in series. After filtration, the solution is filled into appropriate vials or containers.

In one embodiment, the liquid pharmaceutical formulations are intended for parenteral administration. Suitable routes of administration include intramuscular, intravenous, subcutaneous, intradermal, intraarticular, intrathecal and the like. The subcutaneous route of administration is one particular route. Mucosal delivery is also particularly suitable. These mucosal routes include, but are not limited to, oral, nasal, sublingual, pulmonary and buccal routes which may include administration of the peptide in liquid, semi-solid or solid form. Administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The compounds may be provided in dosage unit form containing an amount of the compound that will be effective in one or multiple doses to treat or help in treating the psychiatric disease and/or unwanted side effects of the psychiatric treatment/medication. As will be recognized by those in the field, an effective amount of therapeutic agent will vary with many factors including the age and weight of the patient, the patient's physical condition, the condition to be treated, and other factors.

However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 µg to 1 mg of the compound per dose. Thus, exemplary doses may be 30, 60, 120, 240, or 360 µg of the compound per dose. The doses per day may be delivered in discrete unit doses or provided continuously in a 24 hour period, or any portion of that 24 hour period. The number of doses per day may be from 1 to about 4 doses per day, although it could be more. Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c may be about 6 µg to about 16 or 24 mg per day.

The following Examples are provided to illustrate, but not limit, the invention.

EXAMPLES

Example 1

Male, Sprague-Dawley® rats were submitted to a sugar withdrawal paradigm and observed for effects of stress on sugar intake. Briefly, rats were implanted with ALZET® osmotic pumps containing vehicle or rat amylin (300 µg/kg/d). All rats were provided with ad libitum access to standard chow, water, and a 30% sucrose drink. Subsequently, the sucrose drink was removed and half of the rats were subjected, daily, to 3 h of mild restraint stress for 3 successive days. After 3 days, sucrose was provided and its daily average consumption was measured over 4 days. Chow intake was also measured over the 3 days of withdrawal and stress and over the following 4 days when sucrose was re-introduced.

No restraint was applied during the 4 days of sucrose reintroduction. Results of this assay are shown in FIG. 1 where * is P<0.05 by ANOVA and Fisher LSD post-hoc analyses.

In this model, chronic stress stimulates the proportion of total calories taken in as sugar. As shown in FIG. 1A, stress induced by restraint significantly increased the average sucrose to chow consumption ratio (as % of baseline) (saline, R) over control consumption without stress inducement (saline, C). FIG. 1A also shows that amylin administration prevents the increase in the average sucrose to chow consumption ratio expected as a result of the stress induced by restraint. Compare the sucrose to chow ratio (expressed as a percentage of baseline) between amylin-administered stress-induced rats (amylin, R) and amylin-administered non-stressed control rats (amylin, C). Also compare the sucrose to chow ratio between amylin-administered stress-induced rats (amylin, R) and control vehicle (saline)-administered stress-induced rats (saline, R). As shown, amylin administration reduces this stress-induced response. Accordingly, amylin administration appears to reduce or protect against stress and its effects.

Figure 1B:
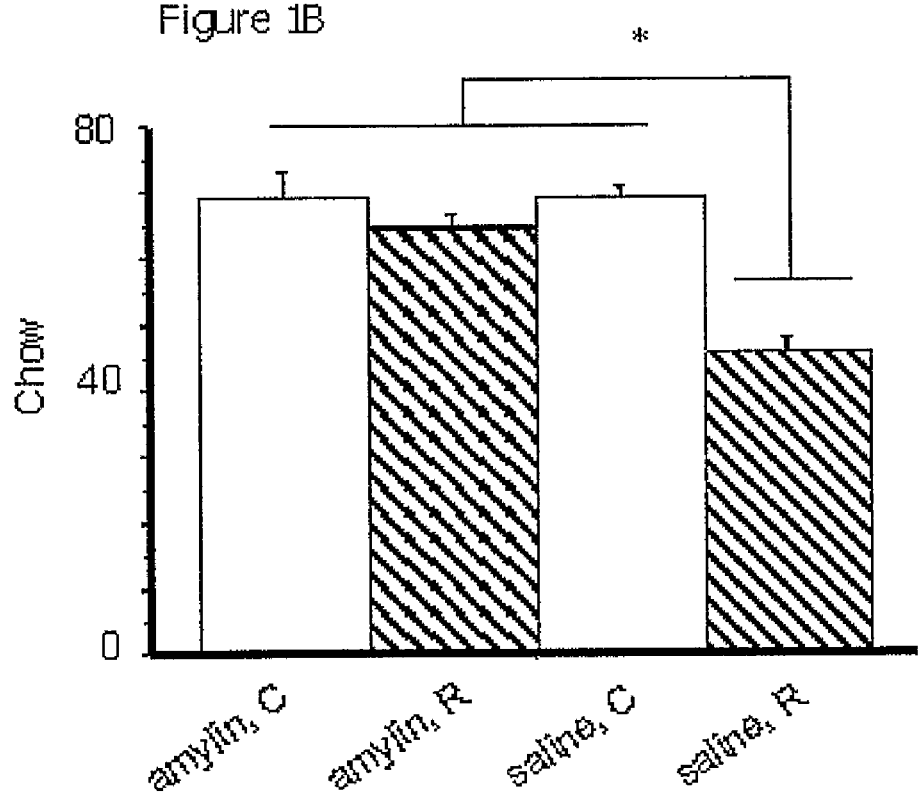

FIG. 1B depicts the same results from the restraint stress assay from a different perspective, that of chow consumption. It is believed that while stress increases palatable feeding (e.g., simple sugars), stress decreases consumption of less palatable foods (e.g., standard chow), a typical response to stress. In line with this belief, stress without amylin administration significantly decreased chow consumption in animals undergoing the stress of restraint. Compare, for example, the chow consumption between saline-treated, restrained animals and saline-treated, control animals in FIG. 1B. Amylin administration also protects against this behavioral response to stress, as indicated by the food intake data in FIG. 1B.

As previously described, the acute effect of stress on food intake is mediated by a central CFR pathway (Smagin et al. (1999) *Am. J. Physiol.* 276:R1461-1468). This result may have behavioral implications since CRF administered into the brain of animals causes anxiety (Dunn et al. (1990) *Brain Res. Brain Res. Rev.* 15:71-100), and chronic stress and the associated increase in central CRF activity are believed to play a critical role in the development of clinical depression and anxiety disorders (Chrousos (2000) *Int. J. Obes. Relat. Metab. Disord.* 24:S50-S55; Koob (1999) *Biol. Psychiatry* 46:1167-1180). Hence, amylin appears to impact a central stress pathway known to mediate behavioral states like depression and anxiety and may be of use as a therapeutic to treat the same.

Example 2

To confirm the interpretation of the findings outlined under Example 1, a variety of animal behavior assays were performed to test for anxiolytic, antidepressant, and antipsychotic effects of amylin administration. The behavioral assays performed use art-accepted, animal models that demonstrate properties characteristic of the respective clinical condition (e.g., anxiety, depression, schizophrenia, obsessive-compulsive disorder) and hence, show face validity. These specific behavioral tests are known to be sensitive to anxiolytic, antidepressant, or antipsychotic drugs. For these assays, rat amylin was administered to mice at doses ranging from 0.1 to 10 mg/kg, intraperitoneally or via a subcutaneously implanted osmotic pump (ALZET®) containing vehicle or rat amylin, and their performance in the assay was assessed.

Stress-Induced Hyperthermia

Figure 2:
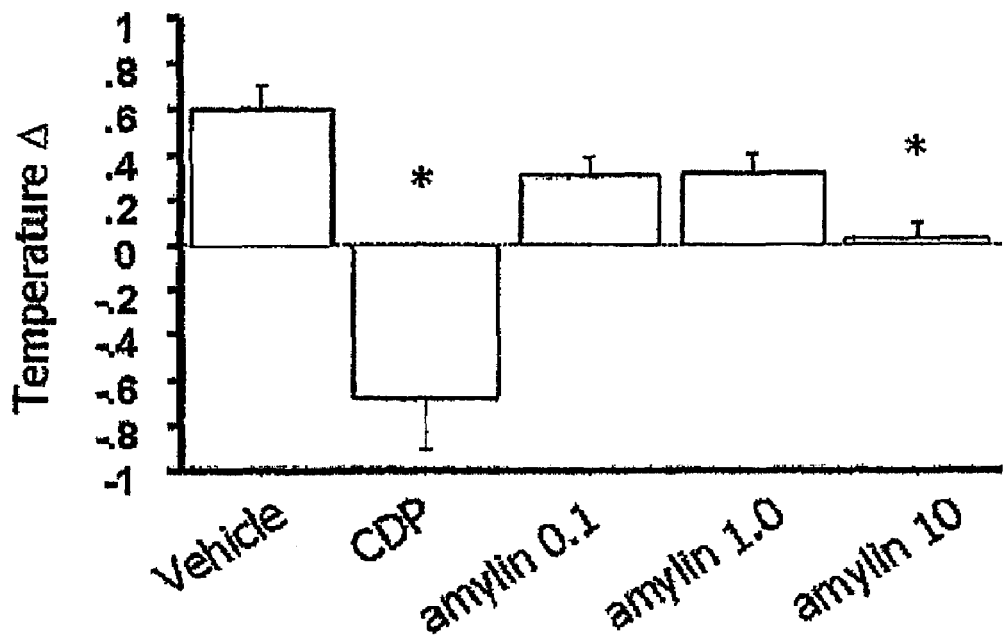
FIG. 2 is a graph depicting the effect of amylin and control agents on stress-induced hyperthermia in mice.

Body temperature and emotional state are closely related in humans, and stress-induced hyperthermia (SIH) in mice is considered to have predictive validity for certain human anxiety/stress disorders. The SIH assay assesses the effect of anxiolytics or test agents on stress-induced hyperthermia and measures the intrinsic effects of these drugs on core body temperature of the animal. See, for example, Zethof et al. (1994) *Physiol. Behav.* 55:109-115. Anxiolytics blunt the increase in body temperature, or hyperthermic response, following stress exposure. The animals were treated with rat amylin (0.1, 1.0 or 10 mg/kg) or control agents (vehicle or 10 mg/kg chlordiazepoxide) 60 minutes before the assay. Mice were subjected to two sequential rectal temperature measurements ten minutes apart. The stress from the first measurement induces hyperthermia which was measured by the second temperature measurement. The difference between the two temperatures ($\Delta T$) was the stress-induced hyperthermia. Results of this assay are shown in FIG. 2 where * is P<0.05. As shown in FIG. 2, administration amylin, like that of the anxiolytic positive control, chlordiazepoxide (CDP), blunted the SIH response. The SIH test results demonstrate the anxiolytic activity of amylin administration. Amylin was also administered chronically at 300 µg/kg/d via subcutaneously implanted pumps and the animals were subjected to the SIH test. At both 1 week and 4 weeks of administration, chronic amylin infusion significantly blunted the SIH response, as did chronically infused CDP at 10 mg/kg/d.

Marble Burying

Figure 3:
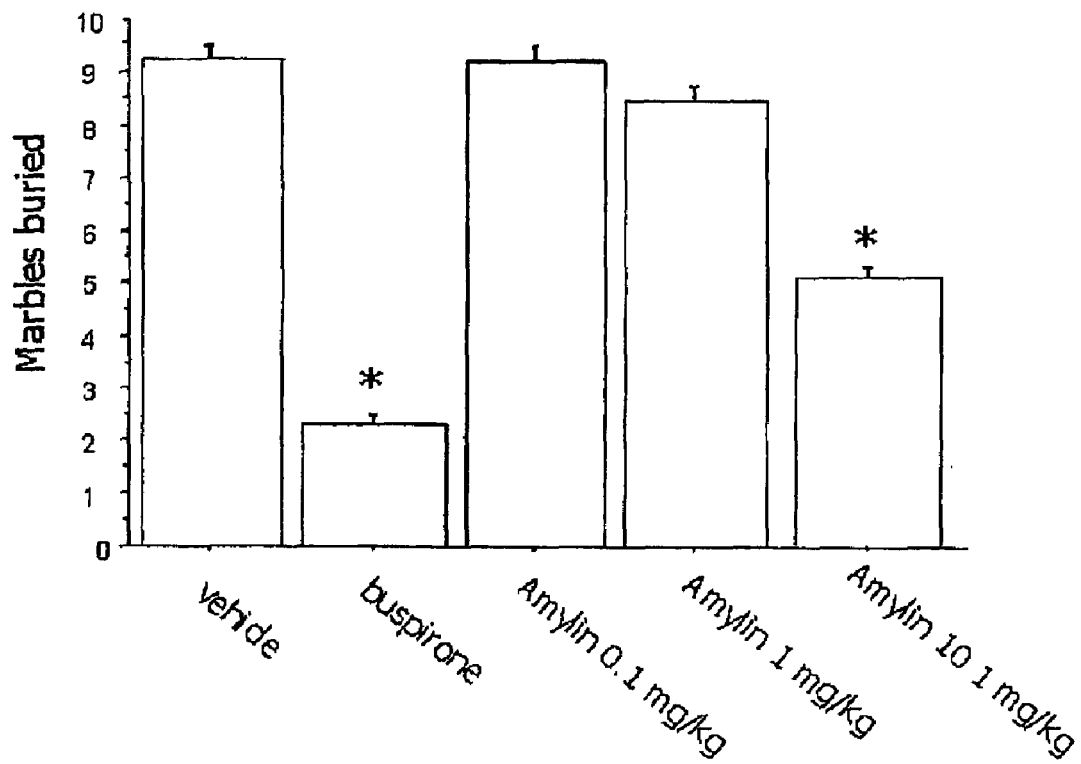
FIG. 3 is a graph depicting the effect of amylin and control agents on marble burying.

Marble burying is used as a model for both anxiety and obsessive-compulsive disorder. See, for example, Chaki et al. (2003) *J. Pharmacol. Exp. Ther.* 304:818-826. Anxiolytics suppress marble burying activity. Mice were injected with the test agent (rat amylin at 0.1, 1.0 or 10 mg/kg, 20/kg buspirone, or vehicle) 15-30 minutes prior to the test. Mice were then placed individually in clean cages containing 5-cm of hard wood bedding and 20 marbles spaced evenly in rows of five. The number of marbles buried in 30 minutes was recorded. Results of this assay are shown in FIG. 3 where * is P<0.05. As shown in FIG. 3, administration of amylin, like that of the anxiolytic positive control, buspirone, reduced the number of marbles buried. The reduction in marble burying with amylin at 10 mg/kg and buspirone at 20 mg/kg were statistically significant. Buspirone is a partial 5-HT1A agonist and an known anxiolytic agent. The marble burying assay results demonstrate the anxiolytic activity and the anti-obsessive compulsive activity of amylin administration.

Forced Swim Test

Figure 4:
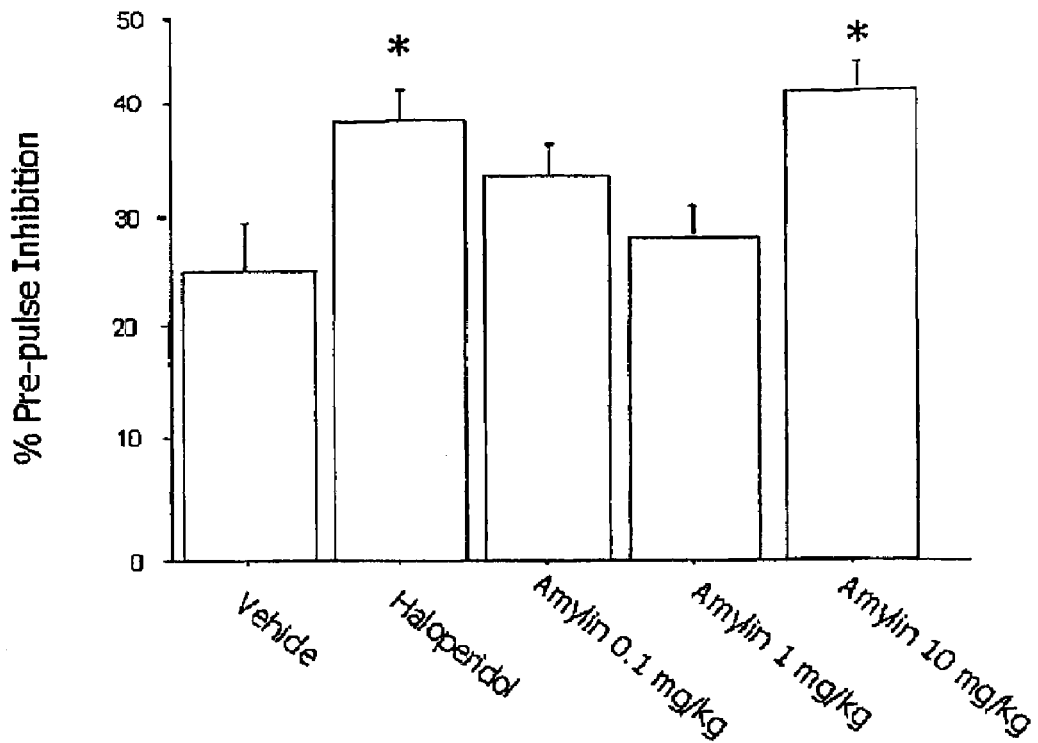
FIG. 4 is a graph depicting the effect of amylin and vehicle control on animals undergoing the forced swim test.

The forced swim test (FST) is a commonly used paradigm to evaluate antidepressant activity of drugs. This test is based on measurement of the animal's floating time in a tank filled with water. When rats or mice are forced to swim in a deep cylinder with tepid water they become nearly immobile and cease trying to escape. This characteristic immobile posture is thought to reflect a depressive-like state and is readily influenced by a wide variety of antidepressants. See, for example, Hédou et al. (2001) *Pharmacol., Biochem. Behav.* 70:65-76, Chaki et al. (2003) *J. Pharmacol. Exp. Ther.* 304:818-826, and Porsolt et al. (1977) *Nature* 266:730-732. Antidepressants decrease the immobility time in the FST. Rat amylin or vehicle was delivered continuously for two weeks to mice by subcutaneously implanted osmotic pumps prior to the FST. On day one, the mice were placed in the water tank for a 15 minute pre-swim session. On day two, the mice were placed back into the water tank for assessment of climbing, swimming, and immobility over a 5 minute trial session. Results of the FST are shown in FIG. 4 where * is P<0.05. As shown in FIG. 4, administration of rat amylin significantly reduced the time spent in the immobile state. Accordingly, the FST results demonstrate the antidepressant activity of amylin administration.

Prepulse Inhibition

The prepulse inhibition (PPI) test measures the reflex response to externally applied auditory stimulation (acoustic startle response) and is related to the deficiency in sensorymotor gating capacity seen in schizophrenia. The acoustic startle reflex is a very basic response to strong exteroceptive stimuli and is widely used to assess sensorimotor reactivity in animals and humans. A weak auditory stimulus (prepulse, 74-82 dB) given prior to the strong acoustic stimulus (120 dB) blunts the startle response. This blunting of the startle response is referred to as prepulse inhibition. See, for example, Conti et al. (2005) Behavioral Neuroscience 119: 1052-1060. Antipsychotics increase the ability of the prepulse stimulus to blunt the startle response to the strong stimulus. Some psychotomimetic agents, such as phencyclidine (PCP) and ketamine, can actually reduce the percent prepulse inhibition and stimulate a psychotic-like state in animals, which can be antagonized by antipsychotic agents.

Figure 5:
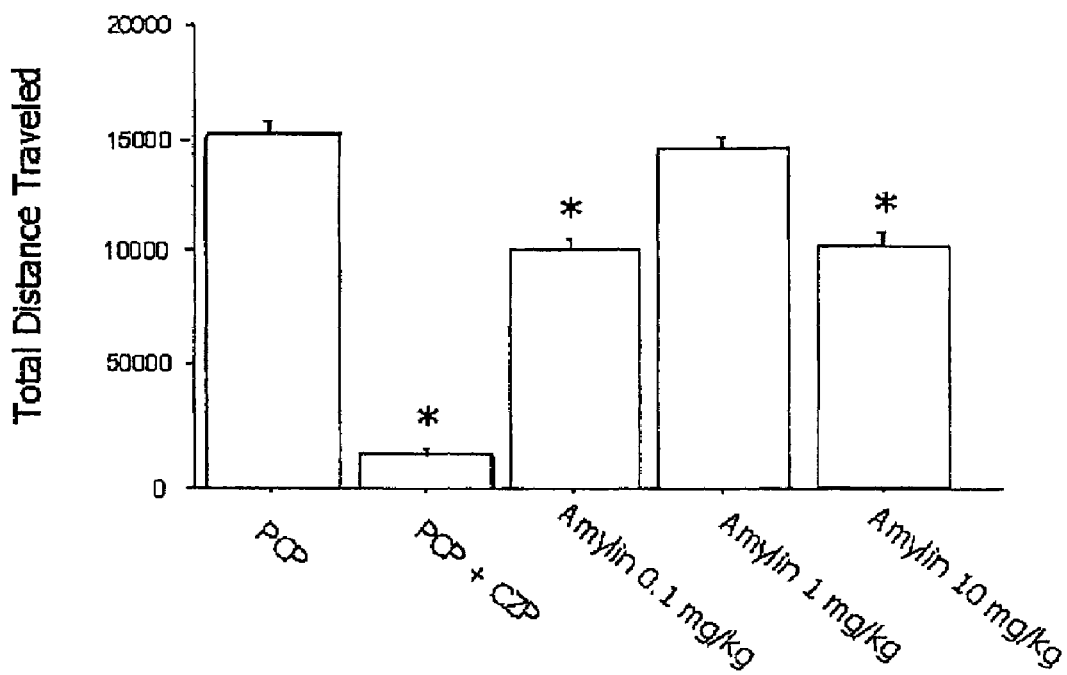
FIG. 5 is a graph depicting the effect of amylin and control agents on prepulse inhibition.

Mice were injected with the test agent (rat amylin at 0.1, 1.0 or 10 mg/kg, or vehicle) 15 prior to the test or with haloperidol at 1 mg/kg 30 minutes prior to the test. The mice were placed into an animal holder and the holder placed onto a transducer platform in an acoustic chamber. A weak auditory stimulus (prepulse) of 74, 78 and 82 dB was given prior to the strong acoustic stimulus (120 dB). The amount of the animal's "reaction" to the strong stimulus was recorded. Results of the PPI assay are shown in FIG. 5 where * is P<0.05. As shown in FIG. 5, administration of amylin at 10 mg/kg, like that of the antipsychotic positive control halperidol, significantly increased the percent of prepulse inhibition at all prepulse levels tested (74, 78, and 82 dB). Halperidol is a dopamine receptor antagonist and a first generation antipsychotic agent. The PPI test results demonstrate the antipsychotic effects of amylin administration.

Phencyclidine (PCP)-Induced Locomotion

Figure 6:
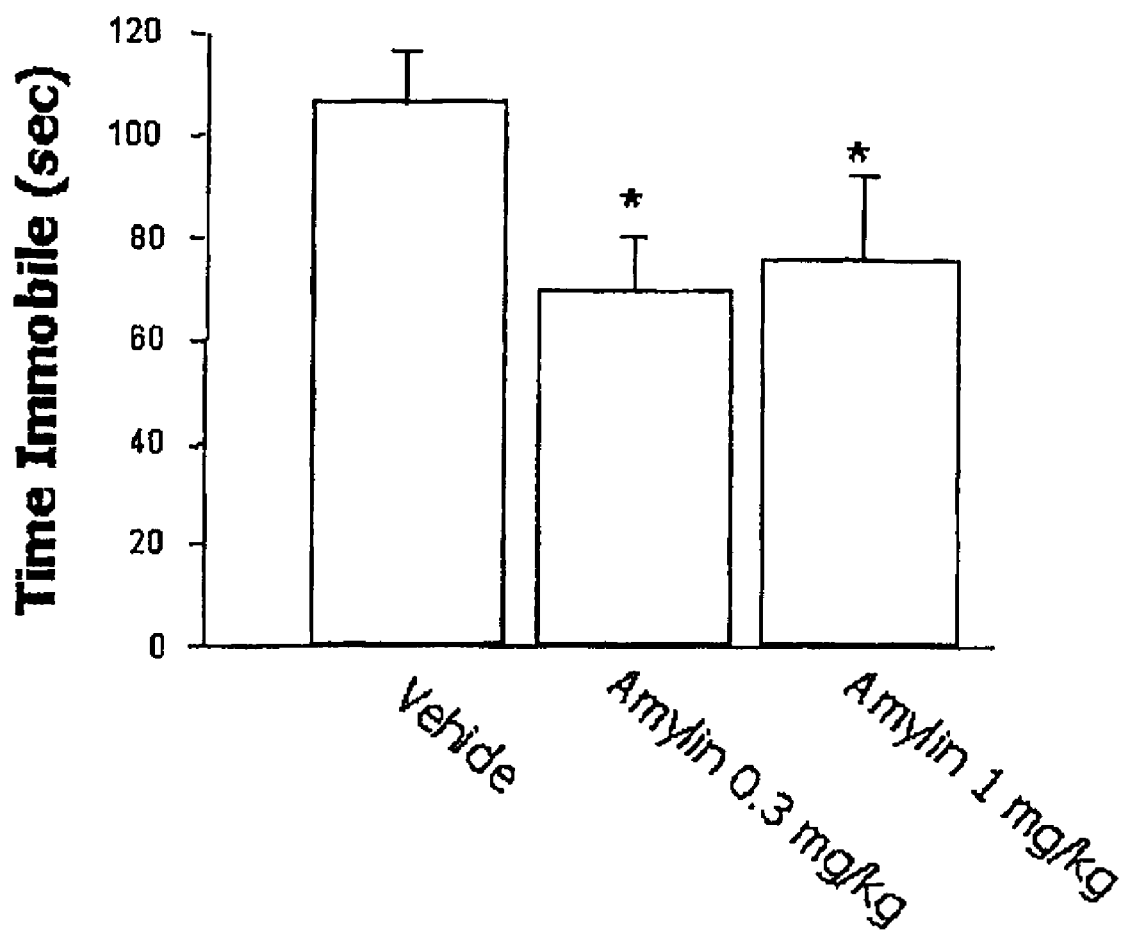
FIG. 6 is a graph depicting the effect of amylin and control agents on phencyclidine (PCP)-induced locomotion.

The PCP-induced locomotion test is used with the open field activity chambers and measures locomotion, rearing, and stereotypic activity under amphetamine/PCP-induced conditions. The test has predictive validity for some antipsychotic drugs that normalize the hyperactivity and stereotypic behavior seen with amphetamine and PCP. See, for example, Williams et al. (2006) Prog. Neuropsychopharmacol. Biol. Psychiatry 30:239-243. Mice were injected with the test agent (rat amylin at 0.1, 1.0 or 10 mg/kg, 3 mg/kg clozapine (CZP), or vehicle) 15-30 minutes prior injection with 5 mg/kg PCP. The animals were then placed in the center of an open field and activity was recorded for 60 minutes. Results of this assay are shown in FIG. 6 where * is P<0.05. As shown in FIG. 6, administration of amylin, like the antipsychotic positive control CZP, significantly reduced the total distance traveled across all types assessed (total, central, and peripheral) in the PCP-induced locomotion test. Amylin, like CZP, reduced rearing activity and PCP-induced rearing activity. Administration of amylin alone did not affect baseline activity whereas CPZ alone did affect baseline activity. CZP is an atypical, second generation antipsychotic drug has a mixed receptor profile, including the dopamine receptor. CPZ has superior antipsychotic activity, with less motor side effects. The PCP-induced locomotion test results demonstrate the antipsychotic activity of amylin administration.

Example 3

Figure 7A:
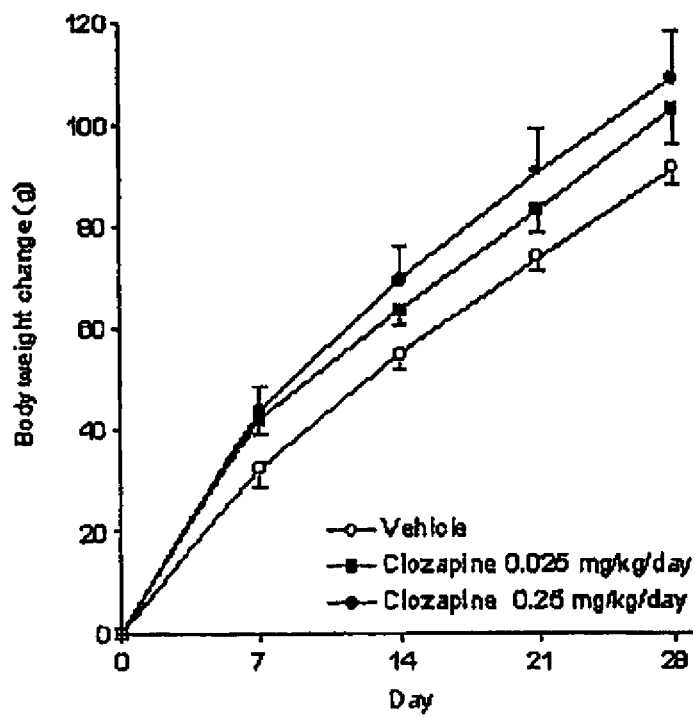
FIGS. 7A and 7B are graphs depicting effects of clozapine on weight. The graph in FIG. 7A depicts the effect of clozapine alone on weight and the graph in FIG. 7B depicts the effect of the combination of clozapine and amylin on weight.
Figure 7B:
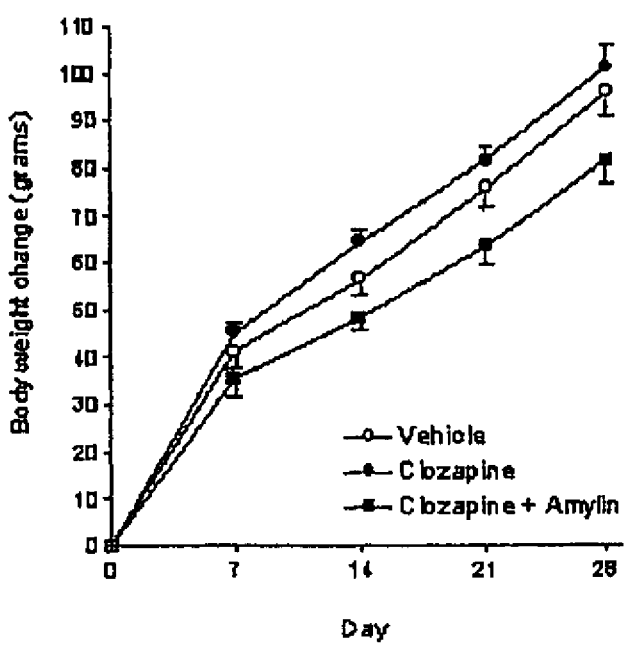

The effect of amylin administration on weight gain induced by the second generation antipsychotic clozapine was examined. Adult, male Sprague-Dawley® rats (diet=58% kcal from fat) were implanted subcutaneously in the interscapular region with osmotic pumps that continuously delivered vehicle or drug for 4 weeks. In one experiment, rats were treated with vehicle or clozapine (0.025 and 0.25 mg/kg/day). In a second experiment, rats were treated with clozapine (0.25 mg/kg/day) or clozapine (0.25 mg/kg/day) in conjunction with rat amylin (10 µg/kg/day). FIG. 7A shows the increased weight gain of clozapine treated-rats compared to vehicle-treated rats. FIG. 7B shows that when amylin was co-administered with clozapine, amylin prevented the weight gain observed in rats treated with clozapine alone.

While the foregoing description discloses the present invention, with examples provided for the purpose of illustration, it will be understood that the practice of the present invention encompasses all of the usual variations, adaptations, or modifications as being within the scope of the claimed invention. Therefore, descriptions and examples should not be construed as limiting the scope of the invention, which is delineated by the appended claims.

What is claimed is:

1. A method for treating depression in a human in need thereof comprising administering to the human a therapeutically effective amount of an amylin agonist analog comprising the amino acid sequence of SEQ ID NO:159 to treat depression.

2. A method for treating depression, an anxiety disorder, or schizophrenia in a subject in need thereof comprising administering to the subject a therapeutically effective amount of an amylin agonist analog having at least 90% sequence identity to the amino acid sequence of SEQ ID NO:159 to treat depression, the anxiety disorder, or schizophrenia.

3. A method for treating depression in a human in need thereof comprising administering to the human a therapeutically effective amount of an amylin agonist analog having at least 95% sequence identity to the amino acid sequence of SEQ ID NO:159 to treat depression.

* * * * *

SEQUENCE LISTING

<160> NUMBER OF SEQ ID NOS: 253

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

```
<210> SEQ ID NO 2
<211> LENGTH: 37
<212> TYPE: PRT
<213> ORGANISM: Rattus sp.

<400> SEQUENCE: 2

Lys Cys Asn Thr Ala Thr Cys Ala Thr Gln Arg Leu Ala Asn Phe Leu
 1               5                  10                  15

Val Arg Ser Ser Asn Asn Leu Gly Pro Val Leu Pro Pro Thr Asn Val
             20                  25                  30

Gly Ser Asn Thr Tyr
         35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Lys, Ala, Ser or not present
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (13)..(13)
<223> OTHER INFORMATION: Ala, Ser or Thr
<220> FEATURE:
<221> NAME/KEY: MOD_RES
<222> LOCATION: (17)..(17)
<223> OTHER INFORMATION: Val, Leu or Ile
<220> FEATURE:
<221> NAME/KEY: MOD_RES
<222> LOCATION: (18)..(18)
<223> OTHER INFORMATION: His or Arg
<220> FEATURE:
<221> NAME/KEY: MOD_RES
<222> LOCATION: (19)..(19)
<223> OTHER INFORMATION: Ser or Thr
<220> FEATURE:
<221> NAME/KEY: MOD_RES
<222> LOCATION: (20)..(20)
<223> OTHER INFORMATION: Ser, Thr, Gln or Asn
<220> FEATURE:
<221> NAME/KEY: MOD_RES
<222> LOCATION: (21)..(21)
<223> OTHER INFORMATION: Asn, Gln or His
<220> FEATURE:
<221> NAME/KEY: MOD_RES
<222> LOCATION: (23)..(23)
<223> OTHER INFORMATION: Phe, Leu or Tyr
<220> FEATURE:
<221> NAME/KEY: MOD_RES
<222> LOCATION: (25)..(25)
<223> OTHER INFORMATION: Ala or Pro
<220> FEATURE:
<221> NAME/KEY: MOD_RES
<222> LOCATION: (26)..(26)
<223> OTHER INFORMATION: Ile, Val, Ala or Leu
<220> FEATURE:
<221> NAME/KEY: MOD_RES
<222> LOCATION: (28)..(28)
<223> OTHER INFORMATION: Ser, Pro, Leu, Ile or Thr
<220> FEATURE:
<221> NAME/KEY: MOD_RES
```

```
<222> LOCATION: (29)..(29)
<223> OTHER INFORMATION: Ser, Pro or Thr
<220> FEATURE:
<221> NAME/KEY: MOD_RES
<222> LOCATION: (31)..(31)
<223> OTHER INFORMATION: Asn, Asp or Gln
<220> FEATURE:
<223> OTHER INFORMATION: See specification as filed for detailed
      description of substitutions and preferred embodiments

<400> SEQUENCE: 3

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
```

```
<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
            35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
            20                  25                  30

Ser Asn Thr Tyr
            35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
            35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30
```

-continued

Gly Ser Asn Thr Tyr
        35

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Thr Asn Val Gly
            20                  25                  30

Ser Asn Thr Tyr
        35

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

```
Gly Ser Asn Thr Tyr
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
```

```
            20                  25                  30

Gly Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 19

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 21

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

Cys Asn Thr Ala Thr Cys Ala Thr Gln Arg Leu Ala Asn Phe Leu Ile
1               5                   10                  15
```

His Ser Ser Asn Asn Leu Gly Pro Ile Leu Pro Pro Thr Asn Val Gly
                20                  25                  30

Ser Asn Thr Tyr
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 23

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
                20                  25                  30

Gly Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
                20                  25                  30

Gly Ser Asn Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 25

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
                20                  25                  30

Gly Ser Asn Thr Tyr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 26

Lys Cys Asn Thr Ala Thr Cys Ala Thr Gln Arg Leu Thr Asn Phe Leu
1               5                   10                  15

-continued

Val His Ser Ser His Asn Leu Gly Ala Ala Leu Leu Pro Thr Asp Val
            20                  25                  30

Gly Ser Asn Thr Tyr
            35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 27

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
            35

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
            35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
            35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Lys Cys Asn Thr Ala Thr Cys Ala Thr Gln Arg Leu Thr Asn Phe Leu

```
                1               5                  10                 15
Val Arg Ser Ser His Asn Leu Gly Ala Ile Leu Pro Pro Thr Asp Val
                    20                  25                 30

Gly Ser Asn Thr Tyr
            35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Lys Cys Asn Thr Ala Thr Cys Ala Thr Gln Arg Leu Thr Asn Phe Leu
1               5                   10                 15

Val Arg Ser Ser His Asn Leu Gly Pro Ala Leu Pro Pro Thr Asp Val
                    20                  25                 30

Gly Ser Asn Thr Tyr
            35

<210> SEQ ID NO 32
<211> LENGTH: 47
<212> TYPE: PRT
<213> ORGANISM: Homo sapiens

<400> SEQUENCE: 32

Thr Gln Ala Gln Leu Leu Arg Val Gly Cys Val Leu Gly Thr Cys Gln
1               5                   10                 15

Val Gln Asn Leu Ser His Arg Leu Trp Gln Leu Met Gly Pro Ala Gly
                    20                  25                 30

Arg Gln Asp Ser Ala Pro Val Asp Pro Ser Ser Pro His Ser Tyr
            35                  40                  45

<210> SEQ ID NO 33
<211> LENGTH: 48
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(9)
<223> OTHER INFORMATION: May or may not be present
<220> FEATURE:
<221> NAME/KEY: MOD_RES
<222> LOCATION: (10)..(10)
<223> OTHER INFORMATION: Met, Ser, Cys, substituted Leu, Lys, Asp or Glu
<220> FEATURE:
<221> NAME/KEY: MOD_RES
<222> LOCATION: (11)..(11)
<223> OTHER INFORMATION: Val, Asp, Leu, Gly, Asn, Ala or Ser
<220> FEATURE:
<221> NAME/KEY: MOD_RES
<222> LOCATION: (12)..(12)
<223> OTHER INFORMATION: Val, Asp, Leu, Gly, Asn, Ala, Ser or Thr
<220> FEATURE:
<221> NAME/KEY: MOD_RES
<222> LOCATION: (13)..(13)
<223> OTHER INFORMATION: Val, Asp, Leu, Gly, Asn, Ala or Ser
<220> FEATURE:
<221> NAME/KEY: MOD_RES
<222> LOCATION: (14)..(14)
<223> OTHER INFORMATION: Val, Asp, Leu, Gly, Asn, Ala, Ser or not
      present
<220> FEATURE:
```

```
<221> NAME/KEY: MOD_RES
<222> LOCATION: (15)..(15)
<223> OTHER INFORMATION: Thr, Ser, Hse, Ahb or Ahp
<220> FEATURE:
<221> NAME/KEY: MOD_RES
<222> LOCATION: (16)..(16)
<223> OTHER INFORMATION: Met, Ser, Cys, substituted Leu, Lys, Asp or Glu
<220> FEATURE:
<221> NAME/KEY: MOD_RES
<222> LOCATION: (29)..(33)
<223> OTHER INFORMATION: Met, Gly, Pro, Ala or not present
<220> FEATURE:
<221> NAME/KEY: MOD_RES
<222> LOCATION: (34)..(34)
<223> OTHER INFORMATION: Arg or not present
<220> FEATURE:
<221> NAME/KEY: MOD_RES
<222> LOCATION: (35)..(35)
<223> OTHER INFORMATION: Gln or not present
<220> FEATURE:
<221> NAME/KEY: MOD_RES
<222> LOCATION: (36)..(36)
<223> OTHER INFORMATION: Asp or Glu
<220> FEATURE:
<221> NAME/KEY: MOD_RES
<222> LOCATION: (41)..(41)
<223> OTHER INFORMATION: Asp or Glu
<220> FEATURE:
<223> OTHER INFORMATION: See specification as filed for detailed
      description of substitutions and preferred embodiments

<400> SEQUENCE: 33

Thr Gln Ala Gln Leu Leu Arg Val Gly Xaa Xaa Xaa Xaa Xaa Xaa Xaa
1               5                   10                  15

Gln Val Gln Asn Leu Ser His Arg Leu Trp Gln Leu Xaa Xaa Xaa Xaa
            20                  25                  30

Xaa Xaa Xaa Xaa Ser Ala Pro Val Xaa Pro Ser Ser Pro His Ser Tyr
        35                  40                  45

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 34

Thr Gln Ala Gln Leu Leu Arg Val Gly
1               5

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Gln or not present
<220> FEATURE:
<221> NAME/KEY: MOD_RES
<222> LOCATION: (2)..(2)
<223> OTHER INFORMATION: Val or not present
<220> FEATURE:
<221> NAME/KEY: MOD_RES
<222> LOCATION: (13)..(17)
<223> OTHER INFORMATION: Met, Gly, Pro, Ala or not present
<220> FEATURE:
<221> NAME/KEY: MOD_RES
<222> LOCATION: (18)..(18)
```

```
<223> OTHER INFORMATION: Arg or not present
<220> FEATURE:
<221> NAME/KEY: MOD_RES
<222> LOCATION: (19)..(19)
<223> OTHER INFORMATION: Gln or not present
<220> FEATURE:
<221> NAME/KEY: MOD_RES
<222> LOCATION: (20)..(20)
<223> OTHER INFORMATION: Asp or Glu
<220> FEATURE:
<221> NAME/KEY: MOD_RES
<222> LOCATION: (25)..(25)
<223> OTHER INFORMATION: Asp or Glu
<220> FEATURE:
<223> OTHER INFORMATION: See specification as filed for detailed
      description of substitutions and preferred embodiments

<400> SEQUENCE: 35

Xaa Xaa Gln Asn Leu Ser His Arg Leu Trp Gln Leu Xaa Xaa Xaa Xaa
1               5                   10                  15

Xaa Xaa Xaa Xaa Ser Ala Pro Val Xaa Pro Ser Ser Pro His Ser Tyr
            20                  25                  30

<210> SEQ ID NO 36
<211> LENGTH: 41
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr
        35                  40

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 37

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 38

Cys Val Leu Gly Thr Cys Gln Val Gln Asn Leu Ser His Arg Leu Trp
1               5                   10                  15
```

Gln Leu Met Gly Pro Ala Gly Arg Gln Asp Ser Ala Pro Val Asp Pro
            20                  25                  30

Ser Ser Pro His Ser Tyr
        35

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 39

Gln Val Gln Asn Leu Ser His Arg Leu Trp Gln Leu Met Gly Pro Ala
1               5                   10                  15

Gly Arg Gln Asp Ser Ala Pro Val Asp Pro Ser Ser Pro His Ser Tyr
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 40

Val Gln Asn Leu Ser His Arg Leu Trp Gln Leu Met Gly Pro Ala Gly
1               5                   10                  15

Arg Gln Asp Ser Ala Pro Val Asp Pro Ser Ser Pro His Ser Tyr
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 41

Val Gln Asn Leu Ser His Arg Leu Gln Leu Met Gly Pro Ala Gly Arg
1               5                   10                  15

Gln Asp Ser Ala Pro Val Asp Pro Ser Ser Pro His Ser Tyr
            20                  25                  30

<210> SEQ ID NO 42
<211> LENGTH: 42
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Thr Gln Ala Gln Leu Leu Arg Val Gly Cys Val Leu Gly Thr Cys Gln
1               5                   10                  15

Val Gln Asn Leu Ser His Arg Leu Trp Gln Leu Arg Gln Asp Ser Ala
            20                  25                  30

Pro Val Asp Pro Ser Ser Pro His Ser Tyr
        35                  40

<210> SEQ ID NO 43

```
<211> LENGTH: 40
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 43

Thr Gln Ala Gln Leu Leu Arg Val Gly Cys Val Leu Gly Thr Cys Gln
1               5                   10                  15

Val Gln Asn Leu Ser His Arg Leu Trp Gln Leu Asp Ser Ala Pro Val
            20                  25                  30

Asp Pro Ser Ser Pro His Ser Tyr
        35                  40

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 44

Val Gly Cys Val Leu Gly Thr Cys Gln Val Gln Asn Leu Ser His Arg
1               5                   10                  15

Leu Trp Gln Leu Arg Gln Asp Ser Ala Pro Val Asp Pro Ser Ser Pro
            20                  25                  30

His Ser Tyr
        35

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 45

Cys Val Leu Gly Thr Cys Gln Val Gln Asn Leu Ser His Arg Leu Trp
1               5                   10                  15

Gln Leu Arg Gln Glu Ser Ala Pro Val Glu Pro Ser Ser Pro His Ser
            20                  25                  30

Tyr

<210> SEQ ID NO 46
<211> LENGTH: 48
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 46

Thr Gln Ala Gln Leu Leu Arg Val Gly Cys Ser Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45

<210> SEQ ID NO 47
```

```
<211> LENGTH: 47
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

Thr Gln Ala Gln Leu Leu Arg Val Gly Cys Asn Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 48
<211> LENGTH: 42
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 48

Arg Val Gly Cys Gly Asn Leu Ser Thr Cys Gln Val Gln Asn Leu Ser
1               5                   10                  15

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

<210> SEQ ID NO 49
<211> LENGTH: 47
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Thr Gln Ala Gln Leu Leu Arg Val Gly Cys Asp Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 50
<211> LENGTH: 48
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 50

Thr Gln Ala Gln Leu Leu Arg Val Gly Cys Gly Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45
```

<210> SEQ ID NO 51
<211> LENGTH: 47
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

Thr Gln Ala Gln Leu Leu Arg Val Gly Met Val Leu Gly Thr Met Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 52
<211> LENGTH: 39
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 52

Gly Met Val Leu Gly Thr Met Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 53

Val Gly Met Val Leu Gly Thr Met Gln Val Gln Asn Leu Ser His Arg
1               5                   10                  15

Leu Trp Gln Leu Arg Gln Asp Ser Ala Pro Val Asp Pro Ser Ser Pro
            20                  25                  30

His Ser Tyr
        35

<210> SEQ ID NO 54
<211> LENGTH: 42
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 54

Arg Val Gly Cys Gly Asn Leu Ser Thr Cys Gln Val Gln Asn Leu Ser
1               5                   10                  15

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

```
<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Val Gly Cys Gly Asn Leu Ser Thr Cys Gln Val Gln Asn Leu Ser His
1               5                   10                  15

Arg Leu Trp Gln Leu Arg Gln Asp Ser Ala Pro Val Asp Pro Ser Ser
            20                  25                  30

Pro His Ser Tyr
        35

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 56

Val Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 57

Gly Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 58
<211> LENGTH: 47
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 58

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Glu Ser Ala Pro Val Glu Pro Ser Ser Pro His Ser Tyr
        35                  40                  45
```

```
<210> SEQ ID NO 59
<211> LENGTH: 47
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 59

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Glu Pro Ser Ser Pro His Ser Tyr
        35                  40                  45

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 60

Gly Thr Met Gln Val Gln Asn Leu Ser His Arg Leu Trp Gln Leu Arg
1               5                   10                  15

Gln Asp Ser Ala Pro Val Glu Pro Ser Ser Pro His Ser Tyr
            20                  25                  30

<210> SEQ ID NO 61
<211> LENGTH: 40
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 61

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Glu Pro Ser Ser Pro His Ser Tyr
        35                  40

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 62

Val Gly Cys Val Leu Gly Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 63
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 63

Gly Cys Asn Thr Ala Thr Cys Gln Val Gln Asn Leu Ser His Arg Leu
1               5                   10                  15

Trp Gln Leu Arg Gln Asp Ser Ala Pro Val Glu Pro Ser Ser Pro His
            20                  25                  30

Ser Tyr

<210> SEQ ID NO 64
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 64

Gly Cys Ser Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 65
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 65

Gly Cys Gly Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 66
<211> LENGTH: 34
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 66

Gly Cys Val Leu Gly Thr Cys Gln Val Gln Asn Leu Ser His Arg Leu
1               5                   10                  15

Trp Gln Leu Arg Gln Glu Ser Ala Pro Val Glu Pro Ser Ser Pro His
            20                  25                  30

Ser Tyr

<210> SEQ ID NO 67
<211> LENGTH: 22
<212> TYPE: PRT
```

-continued

```
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Lys, Arg or not present
<220> FEATURE:
<221> NAME/KEY: MOD_RES
<222> LOCATION: (2)..(2)
<223> OTHER INFORMATION: Cys or not present
<220> FEATURE:
<221> NAME/KEY: MOD_RES
<222> LOCATION: (3)..(3)
<223> OTHER INFORMATION: Asn, Gln, Asp or not present
<220> FEATURE:
<221> NAME/KEY: MOD_RES
<222> LOCATION: (4)..(4)
<223> OTHER INFORMATION: Thr, Ser, Met, Val, Leu or Ile
<220> FEATURE:
<221> NAME/KEY: MOD_RES
<222> LOCATION: (5)..(5)
<223> OTHER INFORMATION: Ala, Val or Ser
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (7)..(7)
<223> OTHER INFORMATION: Cys or Ala
<220> FEATURE:
<221> NAME/KEY: MOD_RES
<222> LOCATION: (8)..(8)
<223> OTHER INFORMATION: Ala, Ser, Glu or Val
<220> FEATURE:
<221> NAME/KEY: MOD_RES
<222> LOCATION: (9)..(9)
<223> OTHER INFORMATION: Thr, Ser or Met
<220> FEATURE:
<221> NAME/KEY: MOD_RES
<222> LOCATION: (10)..(10)
<223> OTHER INFORMATION: Gln, Ala or Asn
<220> FEATURE:
<221> NAME/KEY: MOD_RES
<222> LOCATION: (11)..(11)
<223> OTHER INFORMATION: Arg, His or Lys
<220> FEATURE:
<221> NAME/KEY: MOD_RES
<222> LOCATION: (12)..(12)
<223> OTHER INFORMATION: Leu, Ile or Met
<220> FEATURE:
<221> NAME/KEY: MOD_RES
<222> LOCATION: (13)..(13)
<223> OTHER INFORMATION: Ala or Thr
<220> FEATURE:
<221> NAME/KEY: MOD_RES
<222> LOCATION: (14)..(14)
<223> OTHER INFORMATION: Asn, Ala or Gln
<220> FEATURE:
<221> NAME/KEY: MOD_RES
<222> LOCATION: (15)..(15)
<223> OTHER INFORMATION: Phe, Tyr or Trp
<220> FEATURE:
<221> NAME/KEY: MOD_RES
<222> LOCATION: (16)..(16)
<223> OTHER INFORMATION: Leu, Ile or Met
<220> FEATURE:
<221> NAME/KEY: MOD_RES
<222> LOCATION: (17)..(17)
<223> OTHER INFORMATION: Val, Ala, Ile, Met, Leu, PentylGly or
      t-butylGly
<220> FEATURE:
<221> NAME/KEY: MOD_RES
<222> LOCATION: (18)..(18)
<223> OTHER INFORMATION: Arg, Lys, His, Pro or Ala
<220> FEATURE:
<221> NAME/KEY: MOD_RES
```

```
<222> LOCATION: (19)..(19)
<223> OTHER INFORMATION: Ser, Thr, Ala or not present
<220> FEATURE:
<221> NAME/KEY: MOD_RES
<222> LOCATION: (20)..(20)
<223> OTHER INFORMATION: Ser, Arg, Ala, Gly or not present
<220> FEATURE:
<221> NAME/KEY: MOD_RES
<222> LOCATION: (21)..(21)
<223> OTHER INFORMATION: Gly, Tyr or not present
<220> FEATURE:
<221> NAME/KEY: MOD_RES
<222> LOCATION: (22)..(22)
<223> OTHER INFORMATION: Tyr or not present
<220> FEATURE:
<223> OTHER INFORMATION: See specification as filed for detailed
      description of substitutions and preferred embodiments

<400> SEQUENCE: 67

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Asn, Gln or Asp
<220> FEATURE:
<221> NAME/KEY: MOD_RES
<222> LOCATION: (2)..(2)
<223> OTHER INFORMATION: Thr, Ser, Met, Val, Leu or Ile
<220> FEATURE:
<221> NAME/KEY: MOD_RES
<222> LOCATION: (3)..(3)
<223> OTHER INFORMATION: Ala or Val
<220> FEATURE:
<221> NAME/KEY: MOD_RES
<222> LOCATION: (4)..(4)
<223> OTHER INFORMATION: Thr or Ser

<400> SEQUENCE: 68

Xaa Xaa Xaa Xaa
1

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 69

Arg Ser Ser Gly Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
```

-continued

```
<400> SEQUENCE: 70

Lys Ser Ser Gly Tyr
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 71

His Ser Ser Gly Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 72

Pro Ser Ser Gly Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 73

Arg Ser Arg Gly Tyr
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 74

Arg Thr Ser Gly Tyr
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 75

Arg Ala Ser Gly Tyr
1               5

<210> SEQ ID NO 76
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      construct

<400> SEQUENCE: 76

Ala Ser Ser Gly Tyr
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 77

Arg Ser Ala Gly Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 78

His Ser Ala Gly Tyr
1               5

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 79

Arg Ser Gly Tyr
1

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ala, Cys, homoCys, Asp, Glu, Phe, Ile, Leu,
      Lys, homoLys, Arg, homoArg, Ser, Hse, Thr, Gly, Gln, Asn, Met,
      Tyr, Trp, Pro, Hyp, His, Val or not present
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Ala, Asp, Glu, Asn, Gln, Gly, Val Arg, Lys,
      homoLys, homoArg, His, Ile, Leu, Met or not present
<220> FEATURE:
<221> NAME/KEY: MOD_RES
<222> LOCATION: (4)..(4)
<223> OTHER INFORMATION: Ala, Ile, Leu, Ser, Hse, Thr, Val, Met or not
```

```
      present
<220> FEATURE:
<221> NAME/KEY: MOD_RES
<222> LOCATION: (5)..(5)
<223> OTHER INFORMATION: Ala, Ser, Thr, Hse, Tyr, Val, Ile, Leu or Met
<220> FEATURE:
<221> NAME/KEY: MOD_RES
<222> LOCATION: (6)..(6)
<223> OTHER INFORMATION: Thr, Ala, Ser, Hse, Tyr, Val, Ile, Leu or Met
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Ala, Val, Ile, Leu, Phe or Met
<220> FEATURE:
<221> NAME/KEY: MOD_RES
<222> LOCATION: (9)..(9)
<223> OTHER INFORMATION: Leu, Thr, Ser, Hse, Val, Ile or Met
<220> FEATURE:
<221> NAME/KEY: MOD_RES
<222> LOCATION: (10)..(10)
<223> OTHER INFORMATION: Gly, His, Gln, Lys, Arg, Asn, homoLys or
      homoArg
<220> FEATURE:
<221> NAME/KEY: MOD_RES
<222> LOCATION: (11)..(11)
<223> OTHER INFORMATION: Lys, Arg, Gln, Asn, homoLys, homoArg or His
<220> FEATURE:
<221> NAME/KEY: MOD_RES
<222> LOCATION: (12)..(12)
<223> OTHER INFORMATION: Leu, Ile, Val, Phe, Met, Trp or Tyr
<220> FEATURE:
<221> NAME/KEY: MOD_RES
<222> LOCATION: (13)..(13)
<223> OTHER INFORMATION: Ala, Phe, Tyr, Asn, Gln, Ser, Hse or Thr
<220> FEATURE:
<221> NAME/KEY: MOD_RES
<222> LOCATION: (14)..(14)
<223> OTHER INFORMATION: Ala, Asp, Glu, Gly, Asn, Lys, Gln, Arg, His,
      homoArg, or homoLys
<220> FEATURE:
<221> NAME/KEY: MOD_RES
<222> LOCATION: (15)..(15)
<223> OTHER INFORMATION: Ala, Asp, Glu, Phe, Leu, Ser, Tyr, Ile, Val or
      Met
<220> FEATURE:
<221> NAME/KEY: MOD_RES
<222> LOCATION: (16)..(16)
<223> OTHER INFORMATION: Leu, Phe, Met, Val, Tyr or Ile
<220> FEATURE:
<221> NAME/KEY: MOD_RES
<222> LOCATION: (17)..(17)
<223> OTHER INFORMATION: His, Gln, Asn, Ser, Hse, Thr or Val
<220> FEATURE:
<221> NAME/KEY: MOD_RES
<222> LOCATION: (18)..(18)
<223> OTHER INFORMATION: Lys, homoLys, Arg, homoArg, His, Cit or Orn
<220> FEATURE:
<221> NAME/KEY: MOD_RES
<222> LOCATION: (19)..(19)
<223> OTHER INFORMATION: Phe, Leu, Ser, Hse, Val ,Ile, Thr or not
      present
<220> FEATURE:
<221> NAME/KEY: MOD_RES
<222> LOCATION: (20)..(20)
<223> OTHER INFORMATION: His, Arg, Lys, homoArg, homoLys, Asn, Gln or
      not present
<220> FEATURE:
<221> NAME/KEY: MOD_RES
<222> LOCATION: (21)..(21)
<223> OTHER INFORMATION: Thr, Ser, Hse, Val, Ile, Leu, Gln, Asn or not
      present
<220> FEATURE:
<221> NAME/KEY: MOD_RES
<222> LOCATION: (22)..(22)
<223> OTHER INFORMATION: Phe, Leu, Met, Val, Tyr or Ile
```

```
<220> FEATURE:
<221> NAME/KEY: MOD_RES
<222> LOCATION: (23)..(23)
<223> OTHER INFORMATION: Pro or Hyp
<220> FEATURE:
<221> NAME/KEY: MOD_RES
<222> LOCATION: (24)..(24)
<223> OTHER INFORMATION: Pro, Hyp, Arg, Lys, homoArg, homoLys or His
<220> FEATURE:
<221> NAME/KEY: MOD_RES
<222> LOCATION: (25)..(25)
<223> OTHER INFORMATION: Thr, Ser, Hse, Val, Ile, Leu, Phe or Tyr
<220> FEATURE:
<221> NAME/KEY: MOD_RES
<222> LOCATION: (26)..(26)
<223> OTHER INFORMATION: Asn, Gln, Asp or Glu
<220> FEATURE:
<221> NAME/KEY: MOD_RES
<222> LOCATION: (27)..(27)
<223> OTHER INFORMATION: Thr, Val, Ser, Phe, Ile or Leu
<220> FEATURE:
<221> NAME/KEY: MOD_RES
<222> LOCATION: (28)..(28)
<223> OTHER INFORMATION: Gly or Ala
<220> FEATURE:
<221> NAME/KEY: MOD_RES
<222> LOCATION: (29)..(29)
<223> OTHER INFORMATION: Ser, Hse, Thr, Val, Ile, Leu or Tyr
<220> FEATURE:
<221> NAME/KEY: MOD_RES
<222> LOCATION: (30)..(30)
<223> OTHER INFORMATION: Glu, Gly, Lys, Asn, Asp, Arg, homoArg,
      homoLys, His or Gln
<220> FEATURE:
<221> NAME/KEY: MOD_RES
<222> LOCATION: (31)..(31)
<223> OTHER INFORMATION: Ala, Thr, Ser, Hse, Val, Ile, Leu, Phe or Tyr
<220> FEATURE:
<221> NAME/KEY: MOD_RES
<222> LOCATION: (32)..(32)
<223> OTHER INFORMATION: Phe, Pro, Tyr, Hse, Ser, Thr or Hyp
<220> FEATURE:
<223> OTHER INFORMATION: See specification as filed for detailed
      description of substitutions and preferred embodiments

<400> SEQUENCE: 80

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ala, Cys, Asp, Phe, Ile, Lys, Ser, Thr or not
      present
<220> FEATURE:
<221> NAME/KEY: MOD_RES
<222> LOCATION: (2)..(2)
<223> OTHER INFORMATION: Cys, Asp, Ser or not present
<220> FEATURE:
<221> NAME/KEY: MOD_RES
<222> LOCATION: (3)..(3)
<223> OTHER INFORMATION: Ala, Asp, Asn or not present
<220> FEATURE:
<221> NAME/KEY: MOD_RES
<222> LOCATION: (4)..(4)
<223> OTHER INFORMATION: Ala, Leu, Thr or not present
<220> FEATURE:
```

```
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Thr, Ala, Ser or Val
<220> FEATURE:
<221> NAME/KEY: MOD_RES
<222> LOCATION: (7)..(7)
<223> OTHER INFORMATION: Cys, Lys or Ala
<220> FEATURE:
<221> NAME/KEY: MOD_RES
<222> LOCATION: (8)..(8)
<223> OTHER INFORMATION: Ala, Val, Leu or Met
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His or Gln
<220> FEATURE:
<221> NAME/KEY: MOD_RES
<222> LOCATION: (11)..(11)
<223> OTHER INFORMATION: Lys, Arg, Gln or homoArg
<220> FEATURE:
<221> NAME/KEY: MOD_RES
<222> LOCATION: (12)..(12)
<223> OTHER INFORMATION: Leu, Trp or Tyr
<220> FEATURE:
<221> NAME/KEY: MOD_RES
<222> LOCATION: (13)..(13)
<223> OTHER INFORMATION: Ala, Phe, Asn, Gln, Ser or Thr
<220> FEATURE:
<221> NAME/KEY: MOD_RES
<222> LOCATION: (14)..(14)
<223> OTHER INFORMATION: Ala, Asp, Glu, Gly, Asn, Lys, Gln or Arg
<220> FEATURE:
<221> NAME/KEY: MOD_RES
<222> LOCATION: (15)..(15)
<223> OTHER INFORMATION: Ala, Asp, Glu, Phe, Leu, Ser or Tyr
<220> FEATURE:
<221> NAME/KEY: MOD_RES
<222> LOCATION: (16)..(16)
<223> OTHER INFORMATION: Leu or Phe
<220> FEATURE:
<221> NAME/KEY: MOD_RES
<222> LOCATION: (17)..(17)
<223> OTHER INFORMATION: His, Gln, Ser or Val
<220> FEATURE:
<221> NAME/KEY: MOD_RES
<222> LOCATION: (18)..(18)
<223> OTHER INFORMATION: Lys, Arg, homoArg, Cit or Orn
<220> FEATURE:
<221> NAME/KEY: MOD_RES
<222> LOCATION: (19)..(19)
<223> OTHER INFORMATION: Phe, Leu, Ser or not present
<220> FEATURE:
<221> NAME/KEY: MOD_RES
<222> LOCATION: (20)..(20)
<223> OTHER INFORMATION: His, Gln or not present
<220> FEATURE:
<221> NAME/KEY: MOD_RES
<222> LOCATION: (21)..(21)
<223> OTHER INFORMATION: Thr, Asn or not present
<220> FEATURE:
<221> NAME/KEY: MOD_RES
<222> LOCATION: (22)..(22)
<223> OTHER INFORMATION: Phe, Leu, Met, Val or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
<223> OTHER INFORMATION: Thr or Val
```

```
<220> FEATURE:
<221> NAME/KEY: MOD_RES
<222> LOCATION: (30)..(30)
<223> OTHER INFORMATION: Glu, Gly, Lys or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Pro or Tyr

<400> SEQUENCE: 81

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
                20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ala, Cys, Phe, Ile, Lys, Ser or not present
<220> FEATURE:
<221> NAME/KEY: MOD_RES
<222> LOCATION: (2)..(2)
<223> OTHER INFORMATION: Cys, Asp or Ser
<220> FEATURE:
<221> NAME/KEY: MOD_RES
<222> LOCATION: (3)..(3)
<223> OTHER INFORMATION: Ala, Asp or Asn
<220> FEATURE:
<221> NAME/KEY: MOD_RES
<222> LOCATION: (4)..(4)
<223> OTHER INFORMATION: Ala, Leu or Thr
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (7)..(7)
<223> OTHER INFORMATION: Cys or Lys
<220> FEATURE:
<221> NAME/KEY: MOD_RES
<222> LOCATION: (8)..(8)
<223> OTHER INFORMATION: Ala or Val
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His or Gln
<220> FEATURE:
<221> NAME/KEY: MOD_RES
<222> LOCATION: (11)..(11)
<223> OTHER INFORMATION: Lys, Arg or homoArg
<220> FEATURE:
<221> NAME/KEY: MOD_RES
<222> LOCATION: (13)..(13)
<223> OTHER INFORMATION: Ala, Phe, Asn, Ser or Thr
<220> FEATURE:
<221> NAME/KEY: MOD_RES
<222> LOCATION: (14)..(14)
<223> OTHER INFORMATION: Ala, Asp, Glu, Gly, Asn, Gln or Arg
<220> FEATURE:
<221> NAME/KEY: MOD_RES
```

```
<222> LOCATION: (15)..(15)
<223> OTHER INFORMATION: Ala, Glu, Phe, Leu, Ser or Tyr
<220> FEATURE:
<221> NAME/KEY: MOD_RES
<222> LOCATION: (17)..(17)
<223> OTHER INFORMATION: His, Ser or Val
<220> FEATURE:
<221> NAME/KEY: MOD_RES
<222> LOCATION: (18)..(18)
<223> OTHER INFORMATION: Lys, Arg, homoArg, Cit or Orn
<220> FEATURE:
<221> NAME/KEY: MOD_RES
<222> LOCATION: (19)..(19)
<223> OTHER INFORMATION: Phe, Leu or Ser
<220> FEATURE:
<221> NAME/KEY: MOD_RES
<222> LOCATION: (20)..(20)
<223> OTHER INFORMATION: His or Gln
<220> FEATURE:
<221> NAME/KEY: MOD_RES
<222> LOCATION: (21)..(21)
<223> OTHER INFORMATION: Thr or Asn
<220> FEATURE:
<221> NAME/KEY: MOD_RES
<222> LOCATION: (22)..(22)
<223> OTHER INFORMATION: Phe, Leu, Met, Val or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
<223> OTHER INFORMATION: Thr or Val
<220> FEATURE:
<221> NAME/KEY: MOD_RES
<222> LOCATION: (30)..(30)
<223> OTHER INFORMATION: Glu, Gly, Lys or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Pro or Tyr

<400> SEQUENCE: 82

Xaa Xaa Xaa Xaa Xaa Thr Xaa Xaa Xaa Xaa Xaa Leu Xaa Xaa Xaa Leu
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ala, Cys, Asp, Phe, Lys, Thr or not present
<220> FEATURE:
<221> NAME/KEY: MOD_RES
<222> LOCATION: (2)..(2)
<223> OTHER INFORMATION: Ala, Cys, Asp, Ser or not present
<220> FEATURE:
<221> NAME/KEY: MOD_RES
<222> LOCATION: (3)..(3)
<223> OTHER INFORMATION: Ala, Asp, Asn or not present
<220> FEATURE:
<221> NAME/KEY: MOD_RES
<222> LOCATION: (4)..(4)
<223> OTHER INFORMATION: Ala, Leu, Thr or not present
```

```
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Ala, Ser, Thr or Val
<220> FEATURE:
<221> NAME/KEY: MOD_RES
<222> LOCATION: (7)..(7)
<223> OTHER INFORMATION: Ala, Cys or Lys
<220> FEATURE:
<221> NAME/KEY: MOD_RES
<222> LOCATION: (8)..(8)
<223> OTHER INFORMATION: Ala, Leu, Met or Val
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His or Gln
<220> FEATURE:
<221> NAME/KEY: MOD_RES
<222> LOCATION: (11)..(11)
<223> OTHER INFORMATION: Lys, Gln or Arg
<220> FEATURE:
<221> NAME/KEY: MOD_RES
<222> LOCATION: (12)..(12)
<223> OTHER INFORMATION: Leu, Trp or Tyr
<220> FEATURE:
<221> NAME/KEY: MOD_RES
<222> LOCATION: (13)..(13)
<223> OTHER INFORMATION: Ala, Asn, Gln, Ser or Thr
<220> FEATURE:
<221> NAME/KEY: MOD_RES
<222> LOCATION: (14)..(14)
<223> OTHER INFORMATION: Ala, Asp, Glu, Gly, Lys, Asn, Gln or Arg
<220> FEATURE:
<221> NAME/KEY: MOD_RES
<222> LOCATION: (15)..(15)
<223> OTHER INFORMATION: Ala, Asp, Glu, Phe, Leu, Ser or Tyr
<220> FEATURE:
<221> NAME/KEY: MOD_RES
<222> LOCATION: (16)..(16)
<223> OTHER INFORMATION: Phe or Leu
<220> FEATURE:
<221> NAME/KEY: MOD_RES
<222> LOCATION: (17)..(17)
<223> OTHER INFORMATION: His, Gln, Ser or Val
<220> FEATURE:
<221> NAME/KEY: MOD_RES
<222> LOCATION: (18)..(18)
<223> OTHER INFORMATION: Lys or Arg
<220> FEATURE:
<221> NAME/KEY: MOD_RES
<222> LOCATION: (19)..(19)
<223> OTHER INFORMATION: Phe, Leu, Ser or not present
<220> FEATURE:
<221> NAME/KEY: MOD_RES
<222> LOCATION: (20)..(20)
<223> OTHER INFORMATION: His, Lys, Gln or not present
<220> FEATURE:
<221> NAME/KEY: MOD_RES
<222> LOCATION: (21)..(21)
<223> OTHER INFORMATION: Gln, Thr or not present
<220> FEATURE:
<221> NAME/KEY: MOD_RES
<222> LOCATION: (22)..(22)
<223> OTHER INFORMATION: Phe, Leu or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
```

```
<223> OTHER INFORMATION: Thr or Val
<220> FEATURE:
<221> NAME/KEY: MOD_RES
<222> LOCATION: (30)..(30)
<223> OTHER INFORMATION: Glu, Lys or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Tyr or not present

<400> SEQUENCE: 83

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 84

Leu Gln Thr Tyr
1

<210> SEQ ID NO 85
<211> LENGTH: 32
<212> TYPE: PRT
<213> ORGANISM: Oncorhynchus sp.

<400> SEQUENCE: 85

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 86

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 87

Lys Cys Asn Thr Ala Thr Cys Val Leu Gly Arg Leu Ser Gln Glu Leu
```

```
1               5                   10                  15
His Arg Leu Gln Thr Leu Pro Arg Thr Asn Thr Gly Ser Asn Thr Tyr
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 88

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 89

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 90

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 91

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Asn Val Gly Ser Asn
            20                  25                  30

Thr Tyr

<210> SEQ ID NO 92
<211> LENGTH: 32
<212> TYPE: PRT
```

<213> ORGANISM: Artificial Sequence
<220> FEATURE:
<223> OTHER INFORMATION: Description of Artificial Sequence: Synthetic
      construct

<400> SEQUENCE: 92

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 93

Lys Cys Ala Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 94

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 95

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 96

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr

```
            20                  25                  30

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocap-Ser

<400> SEQUENCE: 97

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 98

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 99

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 100

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 101
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      construct

<400> SEQUENCE: 101

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 102
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 102

Lys Cys Asn Thr Ala Thr Cys Ala Thr Gln Arg Leu Ser Gln Glu Leu
1               5                   10                  15

Arg Lys Leu Gln Thr Tyr Pro Arg Thr Asn Thr Gly Ser Asn Thr Tyr
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 103

Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetyl-Cys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 104

Cys Xaa Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 105
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetyl-Lys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 105

Lys Xaa Asn Thr Ala Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 106
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 106

Ser Thr Ala Val Leu Xaa Lys Leu Ser Gln Glu Leu Xaa Lys Leu Gln
1               5                   10                  15

Thr Tyr Pro Arg Thr Asn Thr Gly Ser Asn Thr Tyr
            20                  25

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
```

```
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 107

Ser Thr Ala Val Leu Xaa Lys Leu Ser Gln Glu Leu Xaa Lys Leu Gln
1               5                   10                  15

Thr Tyr Pro Arg Thr Asn Val Gly Ser Asn Thr Tyr
            20                  25

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 108

Ser Thr Ala Val Leu Xaa Lys Leu Ser Gln Glu Leu Xaa Lys Leu Gln
1               5                   10                  15

Thr Tyr Pro Pro Thr Asn Val Gly Ser Asn Thr Tyr
            20                  25

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
```

```
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 109

Ser Thr Ala Val Leu Xaa Lys Leu Ser Gln Glu Leu Xaa Lys Leu Gln
1               5                   10                  15

Thr Leu Pro Pro Thr Asn Val Gly Ser Asn Thr Tyr
            20                  25

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 110

Lys Cys Asn Thr Ala Thr Cys Leu Leu Gln Gln Trp Gln Lys Leu Leu
1               5                   10                  15

Gln Lys Leu Lys Gln
            20

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 111

Leu Pro Arg Thr Asn Thr Gly Ser Asn Thr Tyr
1               5                   10

<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 112

Lys Cys Asn Thr Ala Thr Cys Leu Leu Gln Gln Leu Gln Lys Leu Leu
1               5                   10                  15

Gln Lys Leu Lys Gln Tyr
            20

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 113

Pro Arg Thr Asn Thr Gly Ser Asn Thr Tyr
1               5                   10

<210> SEQ ID NO 114
```

<211> LENGTH: 32
<212> TYPE: PRT
<213> ORGANISM: Artificial Sequence
<220> FEATURE:
<223> OTHER INFORMATION: Description of Artificial Sequence: Synthetic construct

<400> SEQUENCE: 114

Lys Cys Asn Thr Ala Ser Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic construct

<400> SEQUENCE: 115

Lys Cys Asn Thr Ala Val Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic construct

<400> SEQUENCE: 116

Lys Cys Asn Thr Ala Thr Cys Val Leu Gly Arg Leu Ser Gln Glu Leu
1               5                   10                  15

His Arg Leu Pro Arg Thr Asn Thr Gly Ser Asn Thr Tyr
            20                  25

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic construct

<400> SEQUENCE: 117

Lys Cys Asn Thr Ala Thr Cys Val Leu Gly Arg Leu Ser Gln Glu Leu
1               5                   10                  15

His Leu Pro Arg Thr Asn Thr Gly Ser Asn Thr Tyr
            20                  25

<210> SEQ ID NO 118
<211> LENGTH: 27
<212> TYPE: PRT
<213> ORGANISM: Artificial Sequence
<220> FEATURE:
<223> OTHER INFORMATION: Description of Artificial Sequence: Synthetic construct

<400> SEQUENCE: 118

Lys Cys Asn Thr Ala Thr Cys Val Leu Gly Arg Leu Ser Gln Glu Leu
1               5                   10                  15

```
Tyr Pro Arg Thr Asn Thr Gly Ser Asn Thr Tyr
            20                  25

<210> SEQ ID NO 119
<211> LENGTH: 26
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 119

Lys Cys Asn Thr Ala Thr Cys Val Leu Gly Arg Leu Ser Gln Glu Tyr
1               5                   10                  15

Pro Arg Thr Asn Thr Gly Ser Asn Thr Tyr
            20                  25

<210> SEQ ID NO 120
<211> LENGTH: 25
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 120

Lys Cys Asn Thr Ala Thr Cys Val Leu Gly Arg Leu Ser Gln Tyr Pro
1               5                   10                  15

Arg Thr Asn Thr Gly Ser Asn Thr Tyr
            20                  25

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 121

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: D-Thr

<400> SEQUENCE: 122

Lys Cys Asn Thr Ala Thr Cys Val Leu Gly Arg Leu Ser Gln Glu Leu
```

-continued

```
                1               5                   10                  15
His Arg Leu Gln Thr Tyr Pro Arg Thr Asn Thr Gly Ser Asn Thr Tyr
            20                  25                  30
```

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetyl-Lys
<220> FEATURE:
<221> NAME/KEY: MOD_RES
<222> LOCATION: (11)..(11)
<223> OTHER INFORMATION: Lys(PEG5000)
<220> FEATURE:
<221> NAME/KEY: MOD_RES
<222> LOCATION: (18)..(18)
<223> OTHER INFORMATION: Lys(PEG5000)

<400> SEQUENCE: 123

```
Lys Cys Asn Thr Ala Thr Cys Val Leu Gly Lys Leu Ser Gln Glu Leu
1               5                   10                  15
His Lys Leu Gln Thr Tyr Pro Arg Thr Asn Thr Gly Ser Asn Thr Tyr
            20                  25                  30
```

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetyl-Ala
<220> FEATURE:
<221> NAME/KEY: MOD_RES
<222> LOCATION: (11)..(11)
<223> OTHER INFORMATION: Lys(PEG5000)

<400> SEQUENCE: 124

```
Ala Cys Asn Thr Ala Thr Cys Val Leu Gly Lys Leu Ser Gln Glu Leu
1               5                   10                  15
His Arg Leu Gln Thr Tyr Pro Arg Thr Asn Thr Gly Ser Asn Thr Tyr
            20                  25                  30
```

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetyl-Ala
<220> FEATURE:
<221> NAME/KEY: MOD_RES
<222> LOCATION: (18)..(18)
<223> OTHER INFORMATION: Lys(PEG5000)

<400> SEQUENCE: 125

Ala Cys Asn Thr Ala Thr Cys Val Leu Gly Arg Leu Ser Gln Glu Leu

His Lys Leu Gln Thr Tyr Pro Arg Thr Asn Thr Gly Ser Asn Thr Tyr
            20                  25                  30

<210> SEQ ID NO 126
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 126

Lys Cys Asn Thr Ala Thr Cys Val Leu Gly Arg Leu Ser Gln Glu Leu
1               5                   10                  15

His Arg Leu Gln Thr Leu Gln Thr Tyr Pro Arg Thr Asn Thr Gly Ser
            20                  25                  30

Asn Thr Tyr
        35

<210> SEQ ID NO 127
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 127

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30

Ser Asn Thr Tyr
        35

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 128

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 129

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Synthetic construct

<400> SEQUENCE: 130

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic construct

<400> SEQUENCE: 131

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic construct

<400> SEQUENCE: 132

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (6)..(6)
<223> OTHER INFORMATION: Hse

<400> SEQUENCE: 133

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic

```
                         construct
<220> FEATURE:
<221> NAME/KEY: MOD_RES
<222> LOCATION: (6)..(6)
<223> OTHER INFORMATION: Ahb

<400> SEQUENCE: 134

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Ahp

<400> SEQUENCE: 135

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Thr(OPO3H2)

<400> SEQUENCE: 136

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 137

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 138
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn

<400> SEQUENCE: 138

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Cit
<220> FEATURE:
<221> NAME/KEY: MOD_RES
<222> LOCATION: (18)..(18)
<223> OTHER INFORMATION: Cit

<400> SEQUENCE: 139

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: homoLys
<220> FEATURE:
<221> NAME/KEY: MOD_RES
<222> LOCATION: (18)..(18)
<223> OTHER INFORMATION: homoLys

<400> SEQUENCE: 140

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
```

```
<222> LOCATION: (1)..(1)
<223> OTHER INFORMATION: L-Octylglycine

<400> SEQUENCE: 141

Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: N-3,6-dioxaoctanoly-Lys

<400> SEQUENCE: 142

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 143

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 144

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 145
```

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 146
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (33)..(33)
<223> OTHER INFORMATION: 9Anc

<400> SEQUENCE: 146

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 147
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (33)..(33)
<223> OTHER INFORMATION: L-Octylglycine

<400> SEQUENCE: 147

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: N-isocaproyl-Lys

<400> SEQUENCE: 148

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 149
<211> LENGTH: 32
<212> TYPE: PRT
<213> ORGANISM: Artificial Sequence
<220> FEATURE:

<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: homoArg
<220> FEATURE:
<221> NAME/KEY: MOD_RES
<222> LOCATION: (18)..(18)
<223> OTHER INFORMATION: homoArg

<400> SEQUENCE: 149

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 150

Phe Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 151

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 152

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      construct -continued

```
<400> SEQUENCE: 153

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 154

Lys Cys Asn Thr Ala Thr Cys Ala Thr Gln Arg Leu Ala Asp Phe Leu
1               5                   10                  15

Val His Leu Gln Thr Tyr Pro Thr Asn Val Gly Ser Asn Thr Tyr
            20                  25                  30

<210> SEQ ID NO 155
<211> LENGTH: 29
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 155

Cys Asn Thr Ala Thr Cys Ala Thr Gln Arg Leu Ala Asn Phe Leu Val
1               5                   10                  15

His Leu Gln Thr Tyr Pro Thr Asn Val Gly Ser Asn Thr
            20                  25

<210> SEQ ID NO 156
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 156

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 157

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
            20                  25                  30

<210> SEQ ID NO 158
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 158

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 159

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 160

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 161

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Gly Ser Asn Thr Tyr
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 162

Ala Cys Asn Thr Ala Thr Cys Val Leu Gly Arg Leu Ser Gln Glu Leu
1               5                   10                  15
```

His Arg Leu Gln Thr Tyr Pro Arg Thr Asn Thr Gly Ser Asn Thr Tyr
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 163

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 164

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 165

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 166
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Ser

<400> SEQUENCE: 166

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 167
<211> LENGTH: 32
<212> TYPE: PRT

<213> ORGANISM: Artificial Sequence
<220> FEATURE:
<223> OTHER INFORMATION: Description of Artificial Sequence: Synthetic
      construct

<400> SEQUENCE: 167

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 168

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 169

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 170

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 171

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 172

Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ac-Agy
<220> FEATURE:
<221> NAME/KEY: MOD_RES
<222> LOCATION: (7)..(7)
<223> OTHER INFORMATION: Agy

<400> SEQUENCE: 173

Xaa Ser Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ac-Lys
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 174

Lys Xaa Asn Thr Ala Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 175
<211> LENGTH: 27
<212> TYPE: PRT
<213> ORGANISM: Artificial Sequence
<220> FEATURE:

<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib

<400> SEQUENCE: 175

Ser Thr Ala Val Leu Xaa Arg Leu Ser Gln Glu Leu Arg Leu Gln Thr
1               5                   10                  15

Tyr Pro Arg Thr Asn Thr Gly Ser Gly Thr Pro
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (14)..(14)
<223> OTHER INFORMATION: Lys(For)

<400> SEQUENCE: 176

Ser Thr Ala Val Leu Gly Lys Leu Ser Gln Glu Leu His Lys Leu Gln
1               5                   10                  15

Thr Tyr Pro Arg Thr Asn Thr Gly Ser Gly Thr Pro
            20                  25

<210> SEQ ID NO 177
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 177

```
Ser Thr Ala Val Leu Xaa Lys Leu Ser Gln Glu Leu Xaa Lys Leu Gln
1               5                   10                  15

Thr Tyr Pro Arg Thr Asn Thr Gly Ser Asn Thr Tyr
            20                  25

<210> SEQ ID NO 178
<211> LENGTH: 28
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 178

Ser Thr Ala Val Leu Xaa Lys Leu Ser Gln Glu Leu Xaa Lys Leu Gln
1               5                   10                  15

Thr Tyr Pro Arg Thr Asn Val Gly Ser Asn Thr Tyr
            20                  25

<210> SEQ ID NO 179
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 179

Lys Cys Asn Thr Ala Thr Cys Leu Leu Gln Gln Leu Gln Lys Leu Leu
1               5                   10                  15

Gln Lys Leu Lys Gln Tyr Pro Arg Thr Asn Thr Gly Ser Asn Thr Tyr
                20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 180

Lys Cys Asn Thr Ala Ser Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 181
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 181

Lys Cys Asn Thr Ala Val Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 182
<211> LENGTH: 29
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 182

Lys Cys Asn Thr Ala Thr Cys Val Leu Gly Arg Leu Ser Gln Glu Leu
1               5                   10                  15

His Arg Tyr Pro Arg Thr Asn Thr Gly Ser Asn Thr Tyr
            20                  25

<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 183

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: D-Thr

<400> SEQUENCE: 184

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 185
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: DAh

<400> SEQUENCE: 185

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (18)..(18)
<223> OTHER INFORMATION: Lys(PEG5000)

<400> SEQUENCE: 186

Ala Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 187
<211> LENGTH: 35
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 187

Lys Cys Asn Thr Ala Thr Cys Val Leu Gly Arg Leu Ser Gln Glu Leu
1               5                   10                  15

His Arg Leu Gln Thr Leu Gln Thr Tyr Pro Arg Thr Asn Thr Gly Ser
            20                  25                  30

Asn Thr Tyr
        35

<210> SEQ ID NO 188
<211> LENGTH: 36
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 188

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30

Ser Asn Thr Tyr
        35

<210> SEQ ID NO 189
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 189

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 190

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 191

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 192

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 193

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Hse

<400> SEQUENCE: 194

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Ahb

<400> SEQUENCE: 195

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Ahp

<400> SEQUENCE: 196

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 197
<211> LENGTH: 32
<212> TYPE: PRT

```
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (6)..(6)
<223> OTHER INFORMATION: Thr(OPO3H2)

<400> SEQUENCE: 197

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn

<400> SEQUENCE: 198

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Cit
<220> FEATURE:
<221> NAME/KEY: MOD_RES
<222> LOCATION: (18)..(18)
<223> OTHER INFORMATION: Cit

<400> SEQUENCE: 199

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: homoLys
```

```
<220> FEATURE:
<221> NAME/KEY: MOD_RES
<222> LOCATION: (18)..(18)
<223> OTHER INFORMATION: homoLys

<400> SEQUENCE: 200

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 201
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: L-Octylglycine

<400> SEQUENCE: 201

Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr

<210> SEQ ID NO 202
<211> LENGTH: 31
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: N-3,6-dioxaoctanoyl-Cys

<400> SEQUENCE: 202

Cys Asn Thr Ala Thr Cys Val Leu Gly Arg Leu Ser Gln Glu Leu His
1               5                   10                  15

Arg Leu Gln Thr Val Pro Arg Thr Asn Thr Gly Ser Asn Thr Tyr
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 203

Lys Cys Asn Thr Ala Thr Cys Met Leu Gly Arg Tyr Thr Gln Asp Phe
1               5                   10                  15

His Arg Leu Gln Thr Tyr Pro Arg Thr Asn Thr Gly Ser Asn Thr Tyr
            20                  25                  30

<210> SEQ ID NO 204
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      construct

<400> SEQUENCE: 204

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 205

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 206
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 206

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 207
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (33)..(33)
<223> OTHER INFORMATION: 9Anc

<400> SEQUENCE: 207

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 208
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
```

<222> LOCATION: (33)..(33)
<223> OTHER INFORMATION: L-Octylglycine

<400> SEQUENCE: 208

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 209
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: N-isocaproyl-Lys

<400> SEQUENCE: 209

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: homoArg
<220> FEATURE:
<221> NAME/KEY: MOD_RES
<222> LOCATION: (18)..(18)
<223> OTHER INFORMATION: homoArg

<400> SEQUENCE: 210

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 211

Phe Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 212
<211> LENGTH: 32

```
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (18)..(18)
<223> OTHER INFORMATION: Cit

<400> SEQUENCE: 212

Lys Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (18)..(18)
<223> OTHER INFORMATION: Orn

<400> SEQUENCE: 213

Lys Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 214

Ile Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: 1-Octylglycine

<400> SEQUENCE: 215

Xaa Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 216
```

-continued

```
<211> LENGTH: 31
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Cys

<400> SEQUENCE: 216

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (11)..(11)
<223> OTHER INFORMATION: Cit

<400> SEQUENCE: 217

Lys Cys Asn Thr Ala Thr Cys Val Leu Gly Xaa Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 218
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (33)..(33)
<223> OTHER INFORMATION: 4ABU

<400> SEQUENCE: 218

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 219
<211> LENGTH: 33
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Isocaproyl-Lys
<220> FEATURE:
<221> NAME/KEY: MOD_RES
<222> LOCATION: (33)..(33)
<223> OTHER INFORMATION: 4ABU
```

-continued

<400> SEQUENCE: 219

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 220

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Glu Ala Phe
            20                  25                  30

<210> SEQ ID NO 221
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 221

Lys Cys Asn Thr Ala Thr Cys Val Leu Gly Arg Leu Ser Gln Glu Leu
1               5                   10                  15

His Arg Leu Gln Thr Tyr Pro Thr Asn Val Gly Ser Glu Ala Phe
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 222

Lys Cys Asn Thr Ala Thr Cys Val Leu Gly Arg Leu Ser Arg Ser Leu
1               5                   10                  15

His Arg Leu Gln Thr Tyr Pro Arg Thr Asn Thr Gly Ser Asn Thr Tyr
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 223

Lys Cys Asn Thr Ala Thr Cys Val Thr His Arg Leu Ser Gln Glu Leu
1               5                   10                  15

His Arg Leu Gln Thr Tyr Pro Arg Thr Asn Thr Gly Ser Asn Thr Tyr
            20                  25                  30

```
<210> SEQ ID NO 224
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 224

Lys Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 225

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr
            20                  25                  30

<210> SEQ ID NO 226
<211> LENGTH: 33
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 226

Lys Cys Asn Thr Ala Thr Cys Val Leu Gly Arg Leu Ser Gln Glu Leu
1               5                   10                  15

His Arg Leu Gln Asn Phe Val Pro Arg Thr Asn Thr Gly Ser Asn Thr
            20                  25                  30

Tyr

<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 227

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Glu Thr Phe
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      construct
```

-continued

```
<400> SEQUENCE: 228

Ala Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 229

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Lys Ala Phe
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 230

Lys Cys Asp Thr Ala Thr Cys Val Thr His Arg Leu Ala Gly Leu Leu
1               5                   10                  15

Ser Arg Ser Gln Thr Tyr Pro Arg Thr Asn Thr Gly Ser Asn Thr Tyr
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 231

Lys Cys Asn Thr Ala Thr Cys Val Leu Gly Arg Leu Ala Asp Ala Leu
1               5                   10                  15

His Arg Leu Gln Thr Tyr Pro Arg Thr Asn Thr Gly Ser Asn Thr Tyr
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 232

Lys Cys Asn Thr Ala Thr Cys Val Leu Gly Arg Leu Ala Ala Phe Leu
1               5                   10                  15

His Arg Leu Gln Thr Tyr Pro Arg Thr Asn Thr Gly Ser Asn Thr Tyr
            20                  25                  30

<210> SEQ ID NO 233
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 233

Ser Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 234

Lys Cys Asn Thr Ala Thr Cys Val Leu Gly Arg Leu Ser Gln Glu Leu
1               5                   10                  15

His Arg Leu Gln Thr Met Pro Arg Thr Asn Thr Gly Ser Asn Thr Tyr
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 235

Lys Cys Asn Thr Ala Thr Cys Val Leu Gly Arg Leu Ser Gln Glu Leu
1               5                   10                  15

His Arg Leu Gln Thr Val Pro Arg Thr Asn Thr Gly Ser Asn Thr Tyr
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 236

Lys Cys Asn Thr Ala Thr Cys Val Leu Gly Arg Leu Asn Glu Tyr Leu
1               5                   10                  15

His Arg Leu Gln Thr Tyr Pro Arg Thr Asn Thr Gly Ser Asn Thr Tyr
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 237

Ser Cys Asn Thr Ala Thr Cys Val Leu Gly Arg Leu Ser Gln Glu Leu
1               5                   10                  15
```

-continued

His Arg Leu Gln Thr Tyr Pro Arg Thr Asn Thr Gly Ser Asn Thr Tyr
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 238

Lys Cys Asn Thr Ala Thr Cys Val Leu Gly Arg Leu Thr Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 239

Lys Cys Asn Thr Ala Thr Cys Val Leu Gly Arg Leu Ala Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 240

Lys Cys Asn Thr Ala Thr Cys Val Leu Gly Arg Leu Thr Asp Tyr Leu
1               5                   10                  15

His Arg Leu Gln Thr Tyr Pro Arg Thr Asn Thr Gly Ser Asn Thr Tyr
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 241

Lys Cys Asn Thr Ala Thr Cys Val Leu Gly Arg Leu Ala Gln Phe Leu
1               5                   10                  15

His Arg Leu Gln Thr Tyr Pro Arg Thr Asn Thr Gly Ser Asn Thr Tyr
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

```
<400> SEQUENCE: 242

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Asn Thr Tyr
            20                  25                  30

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 243

Lys Cys Asn Thr Ala Thr Cys Val Leu Gly Arg Leu Ala Asp Phe Leu
1               5                   10                  15

His Arg Phe His Thr Phe Pro Arg Thr Asn Thr Gly Ser Asn Thr Tyr
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 244

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Gly Thr Pro
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 245

Cys Asn Thr Ala Thr Cys Val Leu Gly Arg Leu Ala Asp Phe Leu His
1               5                   10                  15

Arg Leu Gln Thr Tyr Pro Arg Thr Asn Thr Gly Ser Asn Thr Tyr
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 246

Lys Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 247
```

<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 247

Lys Cys Asn Thr Ala Thr Cys Val Leu Gly Arg Leu Phe Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 248

Lys Cys Asn Thr Ala Thr Cys Val Leu Gly Arg Leu Ala Ala Ala Leu
1               5                   10                  15

His Arg Leu Gln Thr Tyr Pro Arg Thr Asn Thr Gly Ser Asn Thr Tyr
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 249

Thr Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 250

Cys Ser Asn Leu Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 251

Lys Cys Asn Thr Ala Thr Cys Ala Thr Gln Arg Leu Ala Asn Glu Leu
1               5                   10                  15

```
Val Arg Leu Gln Thr Tyr Pro Arg Thr Asn Val Gly Ser Asn Thr Tyr
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 252

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 253
<211> LENGTH: 32
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 253

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```